(12) United States Patent
Chuter

(10) Patent No.: US 8,105,372 B1
(45) Date of Patent: Jan. 31, 2012

(54) MODULAR GRAFTING SYSTEM AND METHOD

(75) Inventor: Timothy A. M. Chuter, Atherton, CA (US)

(73) Assignee: Endovascular Technologies, Inc., Menlo Park, CA (US)

(*) Notice: Subject to any disclaimer, the term of this patent is extended or adjusted under 35 U.S.C. 154(b) by 1715 days.

(21) Appl. No.: 10/949,866

(22) Filed: Sep. 24, 2004

Related U.S. Application Data

(62) Division of application No. 09/780,943, filed on Feb. 9, 2001, now Pat. No. 6,814,752.

(60) Provisional application No. 60/187,941, filed on Mar. 3, 2000.

(51) Int. Cl.
*A61F 2/06* (2006.01)

(52) U.S. Cl. .................. 623/1.13; 623/1.11; 623/1.35

(58) Field of Classification Search ............... 623/1.11, 623/1.35, 1.13; 606/153
See application file for complete search history.

(56) References Cited

U.S. PATENT DOCUMENTS

| | | | |
|---|---|---|---|
| 4,501,263 A | 2/1985 | Harbuck | |
| 5,064,435 A | 11/1991 | Porter | |
| 5,211,658 A * | 5/1993 | Clouse | 623/1.14 |
| 5,489,295 A | 2/1996 | Piplani et al. | |
| 5,562,724 A | 10/1996 | Vorwerk et al. | |
| 5,575,817 A | 11/1996 | Martin | |
| 5,578,071 A | 11/1996 | Parodi | |
| 5,628,788 A | 5/1997 | Pinchuk | |
| 5,632,772 A * | 5/1997 | Alcime et al. | 623/1.35 |
| 5,639,278 A | 6/1997 | Dereume et al. | |
| 5,653,743 A | 8/1997 | Martin | |
| 5,676,696 A | 10/1997 | Marcade | |
| 5,676,697 A | 10/1997 | McDonald | |
| 5,683,449 A * | 11/1997 | Marcade | 128/898 |
| 5,709,713 A | 1/1998 | Evans et al. | |
| 5,716,365 A | 2/1998 | Goicoechea et al. | |
| 5,718,724 A | 2/1998 | Goicoechea et al. | |
| 5,723,004 A | 3/1998 | Dereume et al. | |
| 5,741,325 A | 4/1998 | Chaikof et al. | |
| 5,755,769 A | 5/1998 | Richard et al. | |
| 5,776,180 A | 7/1998 | Goicoechea et al. | |
| 5,782,904 A | 7/1998 | White et al. | |
| 5,800,508 A | 9/1998 | Goicoechea et al. | |

(Continued)

FOREIGN PATENT DOCUMENTS

DE 9319267 4/1994

(Continued)

OTHER PUBLICATIONS

Chuter, et al., "Transfemoral Endovascular Aortic Graft Placement", Journal of Vascular Surgery, vol. 18, No. 2, Aug. 1993, pp. 185-197.

(Continued)

*Primary Examiner* — Ryan Severson
*Assistant Examiner* — Julie A Szpira
(74) *Attorney, Agent, or Firm* — Brooks, Cameron & Huebsch, PLLC

(57) ABSTRACT

A system and method for treating and repairing complex anatomy characterized by a plurality of vessel portions oriented at various angles relative to each other. The system including a graft device that is capable of being assembled in situ and has associated therewith a method that avoids the cessation of blood flow to vital organs. A delivery catheter system and various graft supporting, mating and anchoring structures are additionally included.

5 Claims, 20 Drawing Sheets

U.S. PATENT DOCUMENTS

| | | | |
|---|---|---|---|
| 5,824,037 | A | 10/1998 | Fogarty et al. |
| 5,824,042 | A | 10/1998 | Lombardi et al. |
| 5,824,055 | A | 10/1998 | Spiridigliozzi et al. |
| 5,855,598 | A | 1/1999 | Pinchuk |
| 5,916,263 | A | 6/1999 | Goicoechea et al. |
| 5,938,696 | A | 8/1999 | Goicoechea et al. |
| 5,984,955 | A * | 11/1999 | Wisselink ............... 623/1.35 |
| 5,993,481 | A | 11/1999 | Marcade et al. |
| 6,015,431 | A | 1/2000 | Thornton et al. |
| 6,030,414 | A | 2/2000 | Taheri |
| 6,051,020 | A | 4/2000 | Goicoechea et al. |
| 6,099,558 | A | 8/2000 | White et al. |
| 6,102,938 | A | 8/2000 | Evans et al. |
| 6,117,167 | A | 9/2000 | Goicoechea et al. |
| 6,123,722 | A | 9/2000 | Fogarty et al. |
| 6,149,682 | A | 11/2000 | Frid |
| 6,187,033 | B1 * | 2/2001 | Schmitt et al. ............... 623/1.35 |
| 6,210,429 | B1 | 4/2001 | Vardi et al. |
| 6,344,056 | B1 | 2/2002 | Dehdashtian |
| 6,428,565 | B1 * | 8/2002 | Wisselink ............... 623/1.11 |
| 6,579,309 | B1 | 6/2003 | Loos et al. |
| 6,599,302 | B2 * | 7/2003 | Houser et al. ............... 606/153 |
| 6,599,316 | B2 | 7/2003 | Vardi et al. |
| 6,652,567 | B1 | 11/2003 | Deaton |
| 7,014,653 | B2 * | 3/2006 | Ouriel et al. ............... 623/1.14 |
| 7,226,476 | B2 * | 6/2007 | Coppi ............... 623/1.27 |
| 2001/0031920 | A1 * | 10/2001 | Kaufman et al. ............ 600/431 |
| 2006/0155363 | A1 * | 7/2006 | LaDuca et al. ............... 623/1.16 |

FOREIGN PATENT DOCUMENTS

| | | |
|---|---|---|
| FR | 2 678 508 | 1/1993 |
| FR | 2 748 197 | 11/1997 |
| WO | 84/02266 | 6/1984 |

OTHER PUBLICATIONS

Parodi et al., "Transfemoral Intraluminal, Graft Implantation for Abdominal Aortic Aneurysms," Annals of Vascular Surgery, vol. 5, No. 6, 1991, p. 491-499.

Criado et al., "Transluminal Recanalization, Angioplasty and Stenting in Endovascular Surgery: Techniques and Applications," from Greenhalgh, Vascular and Endovascular Surgical Techniques, 3.sup.rd Edition, 1994, pp. 49-70.

Martin et al., "Endoluminal Stented Graft Aorta-Bifemoral Reconstruction," from Greenhalgh, Vascular and Endovascular Surgical Techniques, 3.sup.rd Edition, 1994, pp. 100-104.

May et al., "Transluminal Placement of a Prosthetic Graft-Stent Device for Treatment of Subclavian Artery Aneurysm," Journal of Vascular Surgery, vol. 8, No. 6, Dec. 1993, pp. 1056-1059.

Chuter, T., "Bifurcated Endovascular Graft Insertion for Abdominal Aortic Aneurysm," from Greenhalgh, Vascular and Endovascular Surgical Techniques, 3.sup.rd Edition, 1994, pp. 92-99.

Parodi, J.C., "Transfemoral Intraluminal Graft Implantation for Abdominal Aortic Aneurysms," from Greenhalgh, Vascular and Endovascular Surgical Techniques, 3.sup.rd Edition, 1994, pp. 71-77.

Moore, W.S., "Transfemoral Endovascular Repair of Abdominal Aortic Aneurysm Using the Endovascular Graft System Device," from Greenhalgh, Vascular and Endovascular Surgical Techniques, 3.sup.rd Edition, 1994, pp. 78-92.

* cited by examiner

MODULAR GRAFTING SYSTEM AND METHOD

This application is a divisional of Ser. No. 09/780,943, filed Feb. 9, 2001 now U.S. Pat. No. 6,814,752, which claims the benefit of Provisional Application Ser. No. 60/187,941, filed Mar. 3, 2000.

BACKGROUND OF THE INVENTION

The present invention relates to the treatment or repair of vasculature and more particularly, to delivering a graft device within a blood vessel to address vascular disease.

In recent years, there have been developments in the treatment or repair of the vasculature of humans or other living animals. These developments have been applied to various areas of vasculature to treat a number of conditions such as vessel weakening or narrowing due to disease. The methods developed have involved minimizing the invasive nature of repair so that patient morbidity and mortality can be reduced. The period of recovery has also been reduced with such advances.

Some people are prone to degeneration and dilatation of the aorta, leading to rupture and death from bleeding. A recently-developed method of arterial reconstruction involves the attachment of a tubular conduit (graft) to the non-dilated arteries above and below the degenerated segment using stents; hence the name "stent-graft" for the prosthesis. The lumen of the arterial tree is used as a conduit to the aorta; hence the name "endovascular aneurysm repair" for the procedure.

The procedure is relatively simple when the degenerated segment is without significant branches. The stent-graft needs only one lumen with an orifice at each end. But the procedure is much more complicated when the degenerated segment of the aorta contains branches, because the stent-graft also needs to branch and these branches need to be placed along multiple lines of insertion. The most common, and simplest, example is reconstruction of the aortic bifurcation. This technical hurdle was crossed relatively early. Yet there has been no significant progress in the intervening years towards reconstruction of areas with more branches, such as the suprarenal aorta, the aortic arch, or other complex vasculature near the kidneys or involving the hypogastric, iliac or femoral arteries. The main problem is that the branches are of variable size, variable orientation, and variable position. It is very difficult to create a graft that will mimic the native anatomy, and very difficult to place such a graft in exactly the right orientation and right position without causing ischemia of the vital organs that are fed by the aortic branches. This is especially true of the aortic arch, which has branches to the brain.

The aortic arch, for example, is affected by two degenerative processes, dissection and aneurysmal dilatation, that hitherto have been treated by open surgical reconstruction. The open surgical operation relies upon cardiopulmonary bypass, with or without hypothermic circulatory arrest. The associated mortality, morbidity, debility, pain and expense are all high.

Endovascular methods of reconstruction must deal with certain challenging anatomic features. For example, all three arteries that take origin from the aortic arch supply blood to the brain. Flow through these arteries cannot be interrupted for more than five minutes without risking irreversible neurologic damage. Moreover, the distribution of the arteries in any one patient, and the arch arteries, in particular, is highly variable. It is, therefore, not feasible to mimic this arrangement in every patient without very sophisticated reconstruction. Even if the graft matched the patient's anatomy precisely, it would still be difficult to match the orientation and position of the branches of the graft to the branches of the native vasculature. Additionally, the arch arteries, for example, usually arise from the ascending portion of the arch at acute angles to the downstream aorta. Trans-femoral access to the arch arteries necessitates a sharp change of direction where these arteries arise from the aorta.

However, certain anatomic features lend themselves to endovascular repair. The aorta and in particular, the ascending aorta is long, straight and without significant branches. Further, the aorta is wide and consequently, there would be room for a main or primary graft conduit to lie alongside its branches. Also, it is relatively easy to gain access to the femoral and iliac arteries.

Accordingly, what is needed and heretofore unavailable is a system and method for treating or repairing complex vasculature while minimizing risk and the recovery time of the patient. The present invention meets these and other needs.

SUMMARY OF THE INVENTION

Briefly and in general terms, the present invention is directed to a device and method for treating or repairing diseased vasculature. The invention provides a minimally invasive approach to the treatment of complex vasculature characterized by a first vessel in fluid communication with a plurality of vessel portions extending at various angles from the first vessel. The present invention is also concerned with treating or repairing vessels which are difficult to access and which supply blood to vital organs which require a continuous source of blood and accordingly, avoids complexities associated with simultaneous insertion and deployment of multiple components.

The present invention embodies a graft device having a superior end, an inferior end, a midsection and a plurality of apertures. Each of the apertures of the grafting device are capable of being aligned with or placed in the relative vicinity of a vessel portion to enable an exterior component to extend from the grafting device to the vessel portion to enable an extension component to extend from the grafting device to the vessel portion. In one aspect, the superior and inferior ends of the graft device each include apertures and are configured within a first vessel portion and each of the apertures formed in the midsection are aligned with blood vessel portions extending at an angle from the first vessel. Further, it is contemplated that the graft device includes a main component and a plurality of extension components that are configured to mate with the main component. Various anchoring, mating and support structures are also contemplated that facilitate securing the graft device within vasculature for accomplishing repairing complex vessel anatomy. Occlusion structures are also included that can be used to close off one or more unused graft device apertures.

Additionally, the present invention embodies a delivery catheter system and method that accomplishes the deployment and attachment of the graft device within vasculature. The delivery catheter system includes structure for receiving the various components of the graft device of the present invention as well as a series of guidewires which provide a path taken by components of the delivery catheter system.

It is contemplated that a branched stent-graft of the present invention be constructed in-situ from multiple components, a main or primary stent-graft with multiple short branches and several branch extensions. Variations in arterial anatomy are accommodated intraoperatively through the independent selection of components as indicated by intraoperative measurements.

In one aspect, the device does not attempt to mimic native anatomy. For example, the widest portion of the primary stent-graft is attached (usually with a stent or an anchoring device) to the proximal aorta. All branches of the primary stent-graft originate at a level proximal to the branches of the aorta. The variable gap between branches of the stent-graft and branches of the aorta is accommodated by variation in the length of the extensions. Thus, several extensions run next to one another through the proximal aortic segment. This is possible because the central section of the primary stent-graft is sized to be much smaller than the native aorta in the region of the aortic branches. The space around the central section also allows for blood flow from the stent-graft branches to the aortic branches and continuing perfusion of the vital organs while extensions are added one by one. A distal aortic seal is established through a slightly wider segment. Alternatively, additional components can be added with their own branches to permit extension into other aortic branches, such as the iliac arteries.

The extensions can be fully-stented (lined from one end to the other with stents or some other means of support), yet flexible. As so configured, they maintain a stable position through a combination of stent support and anchoring or attachment mechanisms at both ends.

The two main sites requiring this kind of treatment are the aortic arch and the suprarenal aorta. The present invention also has applications in other complex anatomy including the iliac, hypogastric or femoral arteries. Although the principles are the same for such sites, differences in anatomy necessitate differences in basic technique. For example, in the arch, the extensions are introduced through the branch arteries, while in the suprarenal aorta the extensions are introduced through the stent-graft from a point of peripheral arterial access in the upper body, usually the left upper limb.

In a preferred embodiment of the present invention, the trunk of the primary stent-graft is bone-shaped with three segments; a narrow central segment and wider segments at both ends. The wider segments are large enough to engage the aorta. Typical diameters are 3.5-4.5 cm proximally and 2.5-3.5 cm distally. The central segment is smaller (approx. 2 cm). Three stent-graft limbs or branches arise from the transition zone between the proximal and middle segments. These are also small (approx. 1 cm). Their origins are staggered at 1 cm intervals both down the length of the trunk and around its circumference.

In one embodiment, there is a self-expanding anchoring device or stent in each of the five stent-graft orifices. Flexible bracing wires run along the outer aspect of the stent-graft between all five stents, so that each segment of the stent-graft is held to a fixed length. Guidewires run alongside the central catheter of the delivery system and through the stent-graft, entering through an inferior or distal orifice and exiting through the orifices of the branches to run back down the outer aspect of the stent-graft. At the base of each branch of the stent-graft there are several circumferential suture loops that form part of a stent-graft to stent-graft mating or attachment system.

Long, flexible, narrow, fully-stented stent-graft extensions exist in a range of lengths and diameters. Each has an external grappling mechanism on the outer aspect of the graft near the proximal tip. The inner 2-3 cm of the extension is sized to match the diameter of the primary stent-graft branch (approx. 1 cm). The rest of the extension is sized to match the diameter of the arch artery.

The stent-graft is inserted through a flexible sheath into the arch of the aorta from an access point in the femoral artery. When released from its sheath, the stent-graft expands. A catheter is advanced over one of the guidewires, through the trunk of the stent-graft and out of one of the branches. The guidewire is then withdrawn and directed into a waiting snare that was previously inserted into the aorta through corresponding arch artery. The distal stent-graft branch corresponds to the left subclavian artery, the middle stent-graft branch corresponds to the left carotid artery and the proximal stent-graft branch corresponds to the innominate (brachiocephalic) artery.

The femoro-brachial guidewires are used to insert calibrated catheters into the proximal aorta through the stent-graft branches. Angiography through the calibrated catheter allows the selection of a suitably sized extension. Each calibrated catheter is then exchanged (over the wire) for the delivery systems of the corresponding stent-graft extension. The extension is deployed within the stent-graft branch where it is secured by the friction generated by the outward pressure of its stents and by the interaction of the grappling mechanism with the loops of the stent-graft branch.

In other embodiments, the application of the present invention relates to treating complex vasculature involving the iliac, femoral, and hypogastric arteries. Various approaches are contemplated to accomplish the in-situ assembly of components of the graft device of the present invention.

Other components of the present invention include employing stents with a very high expansion ratio which are flexible and have a low profile. Various methods of accomplishing secure stent-graft to stent-graft attachment are also contemplated as are various methods of providing a graft component with a desired flexibility and radial strength.

These and other objects and advantages of the invention will become apparent from the following more detailed description, when taken in conjunction with the accompanying drawings of illustrative embodiments.

DETAILED DESCRIPTION OF THE PREFERRED EMBODIMENTS

Figure 1:
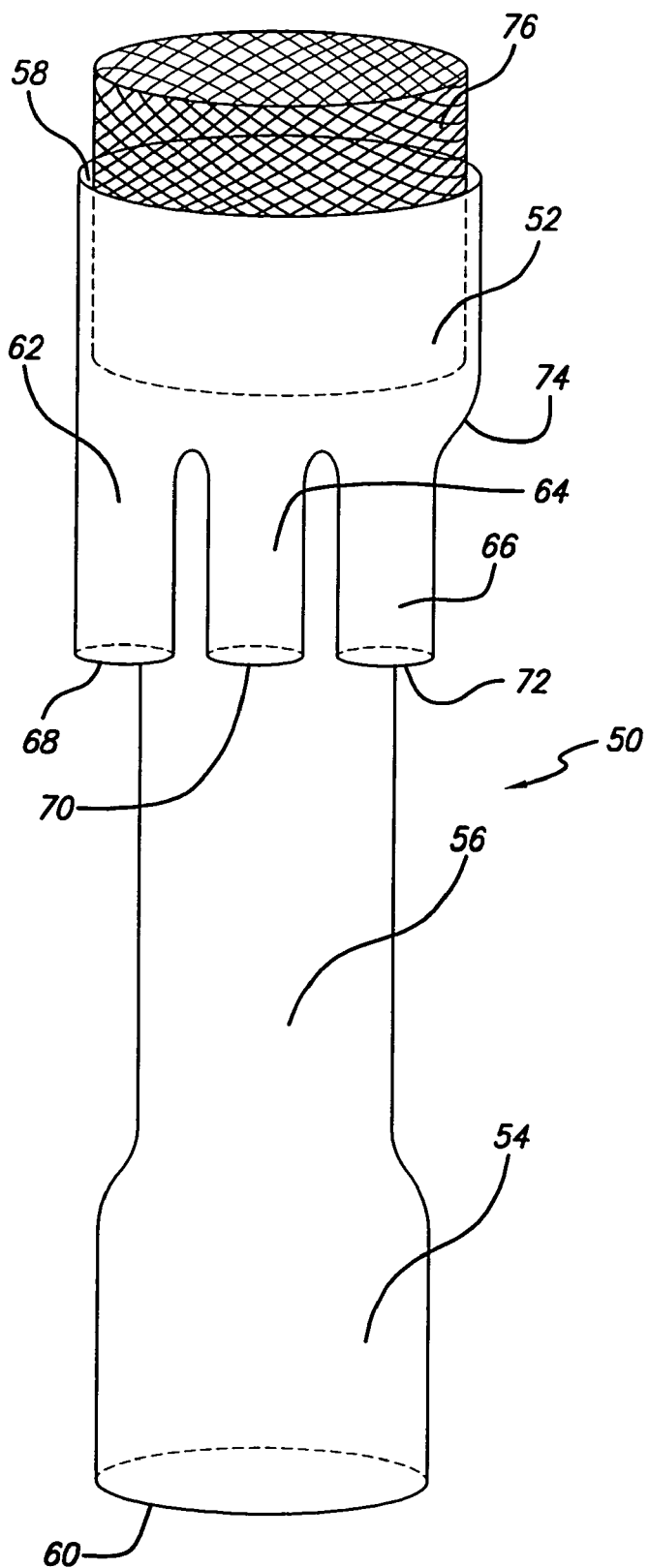
FIG. 1 is a perspective view, depicting one component of a graft device of the present invention.

As shown in the drawings, which are included for purposes of illustration and not by way of limitation, the present invention is embodied in a system and method for treating or repairing complex vasculature that feeds vital body organs. In one aspect of the invention, disease affecting the vasculature proximal the aortic arch is addressed while in other aspects, disease affecting complex vasculature including the thoracic, renal, iliac, femoral or hypogastric arteries is addressed. It is contemplated that an approach involving an in-situ assembly of a modular graft device be employed to treat or repair such vasculature. Accordingly, various anchoring, mating, and support structures are contemplated as well as a delivery catheter system for accomplishing the deployment of the same. Further, the present invention provides a minimally invasive technique for addressing disease by avoiding conventional invasive surgery that has heretofore been required to repair highly complex portions of vasculature.

Referring now to FIG. 1, there is shown one application of the present invention. As shown in FIG. 1, the present invention includes a first or main graft component 50. The main graft component 50 embodies a generally tubular shape involving a superior end portion 52, an inferior end portion 54, and a midsection 56. Each of the superior 52 and inferior 54 end portions includes openings or apertures 58, 60. Additionally, the main graft component 50 includes a plurality of limbs 62, 64, 66 extending in an inferior direction (though they can extend in various and varied other directions) from a superior end portion of the main component 50. Each of the limbs 62, 64, 66 include openings or apertures 68, 70, 72 at terminal ends of the limbs 62, 64, 66. Although the figures depict three such limbs, fewer or more limbs may be provided for a particular purpose. The limbs can be different lengths and can be located at different axial and circumferential locations along the main graft.

To minimize the outer profile of the main component 50 and to otherwise provide a space for the limbs 62, 64, 66 and other components of the present invention, the midsection 56 of the main component 50 is narrowed with respect to the superior 52 and inferior 54 ends. That is, the midsection 56 has a circumference or radial dimension less than that of the superior 52 and inferior 54 ends, whereas the superior 52 and inferior 54 ends can have the same or different circumferences or radial dimensions. A transition section 74 is included medial each of the superior 52 and inferior 54 end portions whereat the circumference of the graft device narrows to that of the midsection 56. The circumference or radial dimension of the limbs 62, 64, 66 is generally less than that of the midsection section 56 and the limbs 62, 64, 66 can have equal or varied circumferences.

The main component can be fabricated by any convention means whether it be assembling separate pieces of graft material into a desired configuration or employing various weaving techniques to thereby have a one piece design. In one preferred approach of manufacture, several tubular pieces of standard vascular material can be attached to each other using suture. Further, the trunk (superior, inferior, and midsection portions) and limbs can embody woven polyester or PTFE folds or areas of double layers of material can be added as required to attach anchoring, grappling or support structures to the graft component.

In the present invention, it is contemplated that the superior end portion 52 be configured with an anchoring device 76 that operates to attach the main component 50 within vasculature. The anchoring device 76 can be placed or attached to an interior or an exterior of the main component 50 and can assume various forms. Additionally, the main component 50 can include support structures extending the entire length or a portion of the length of the main component 50 and various structures for mating with other graft components. The anchoring device can be within the length of the main graft or extend beyond the end of the graft as shown.

Figure 2:
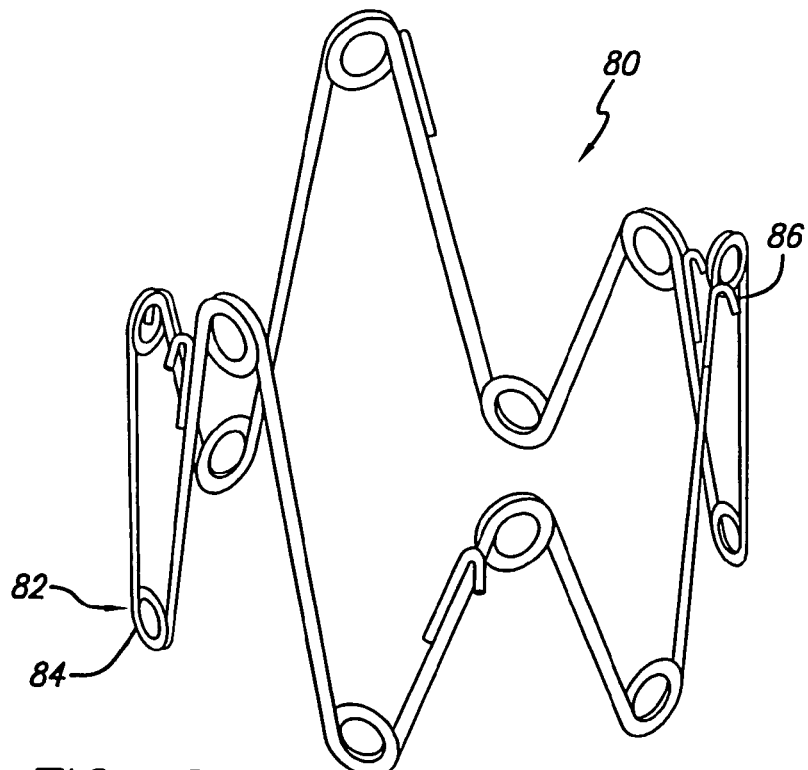
FIG. 2 is a perspective view, depicting one embodiment of an anchoring device of the present invention.
Figure 3:
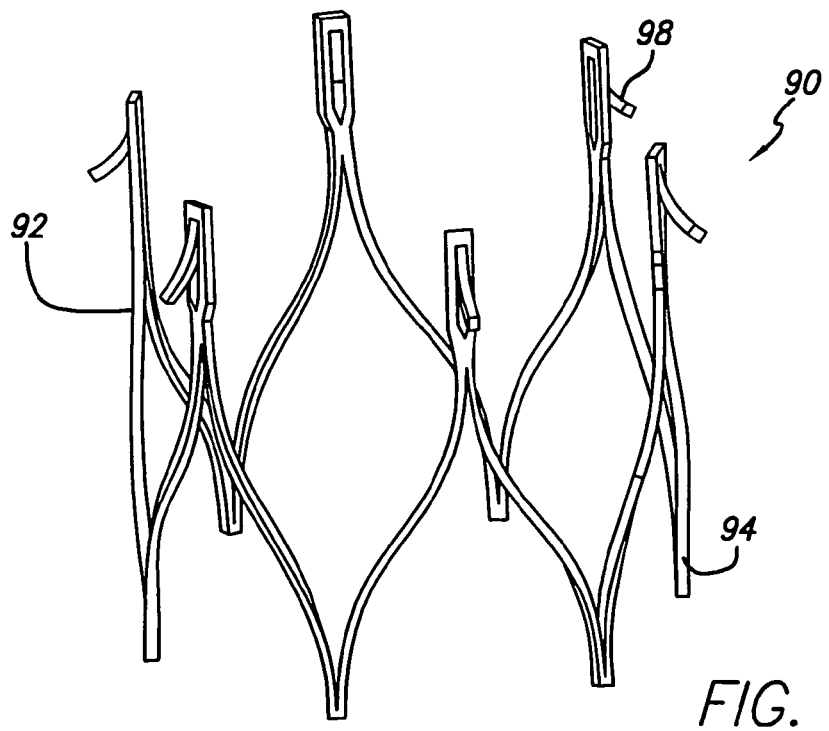
FIG. 3 is a perspective view, depicting a second embodiment of an anchoring device of the present invention.

With reference to FIGS. 2 and 3, there is shown two forms of anchoring devices which may be used, although other forms can be employed as necessary. As shown in FIG. 2, a generally sinusoidal anchoring device 80 including a plurality of alternating apices 82 configured with torsion springs 84 and wall engaging members 86 attached to members 88 connecting the apices 82 is one acceptable device for attaching the graft component 50 within vasculature. Another acceptable anchoring device 90 (FIG. 3) is embodied in a flat wire frame 92 that has alternating apices 94, curved members 96 connecting the apices 94 and wall engaging members 98 extending from selected apices 94. Each of these devices 80, 90 can be attached to any portion of the main component 50 or other components which mate with the main component 50, by sewing or gluing or spot deformation welding, for the purpose of anchoring such graft components to vasculature. Further, these devices 80, 90 can be self-expanding or manufactured so that a radial force is required for expansion.

Figure 4:
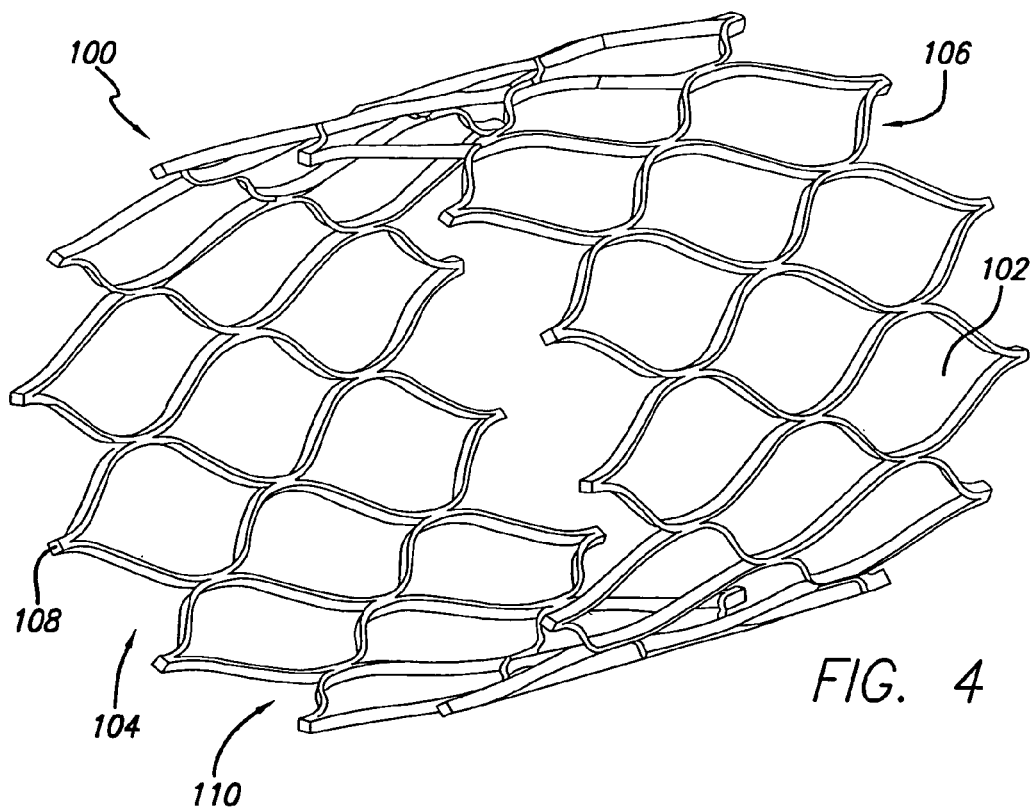
FIG. 4 is a perspective view, depicting a support structure of the present invention.

Moreover, with reference to FIG. 4, the main component 50 or other components mating therewith may include support structure 100 configured about an exterior circumference or internal bore of the particular component. One such support structure 100 may include a flat wire framework defining a plurality of connected and embedded, generally almond-shaped apertures 102. The members 104 defining the almond-shaped apertures 102 are curved in a manner to optimize radial expansion and strength while providing a small profile when compressed. The ends 104, 106 of the support structures 100 is defined by a plurality of apices 108 of the almond-shaped apertures 102 and members 104 defining half-almond shaped gaps 110. Such a support structure 100 can be manufactured to be long enough to support the entire length of a graft component or a plurality of support structures having a desired length can be placed in series along the particular graft component to provide the longitudinal and axial flexibility desired for a particular application. Generally, it is contemplated that the support structure 100 is self-expanding; however, it may be desired that for certain applications, a balloon catheter can be utilized to expand the support structure 100.

It is also contemplated that support structures can embody a modified form of the device shown in FIGS. 2 and 3. That is, acceptable support structures can embody the sinusoidal frame without the wall engaging members 86 of the anchoring device 80 shown in FIG. 2 or the flat wire frame 92, without wall engaging members 98, of the anchoring device 90 shown in FIG. 3. In both cases, a series of such devices can be placed along a selected length of a particular graft component.

Additionally, in other embodiments a bracing device (not shown) in the form of an elongate wire or equivalent structure can be configured between anchoring devices or other support structures attached to a graft component. The bracing device is intended to provide the particular graft component with longitudinal stiffness and pushability Although the anchoring, support, and bracing wire structures can be made from radiopaque material, radiopaque markers can also be added to components of the graft device of the present invention. Such markers can be sewn into material used to manufacture the particular graft component. The radiopaque markers or other radiopaque structures are used during the advancement and deployment of a graft component within diseased vasculature. High resolution imaging is employed to view such a procedure. Fluoroscopy and other remote imaging techniques are also contemplated to accomplish the viewing of the radiopaque structures during an implant procedure.

Figure 5:
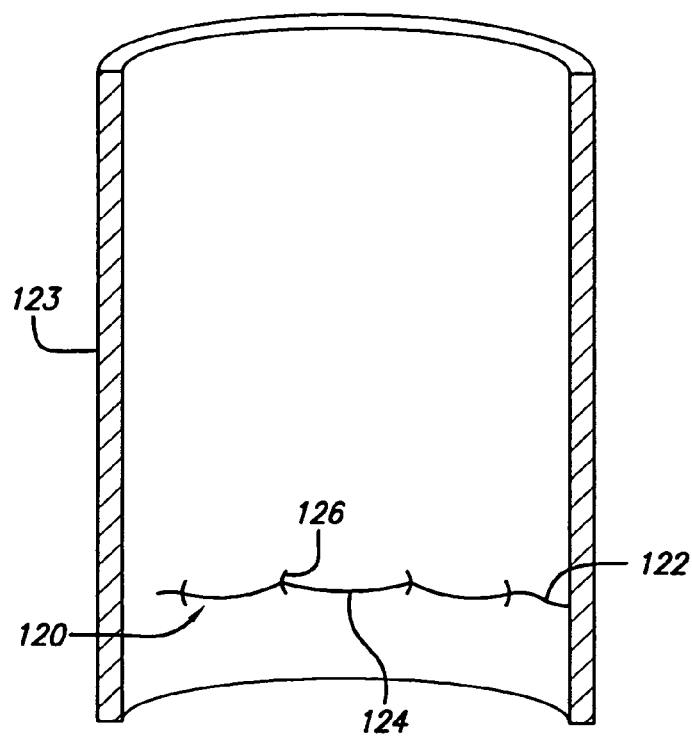
FIG. 5 is a cross-sectional view, depicting one embodiment of mating structures of a component of a graft device of the present invention.
Figure 6:
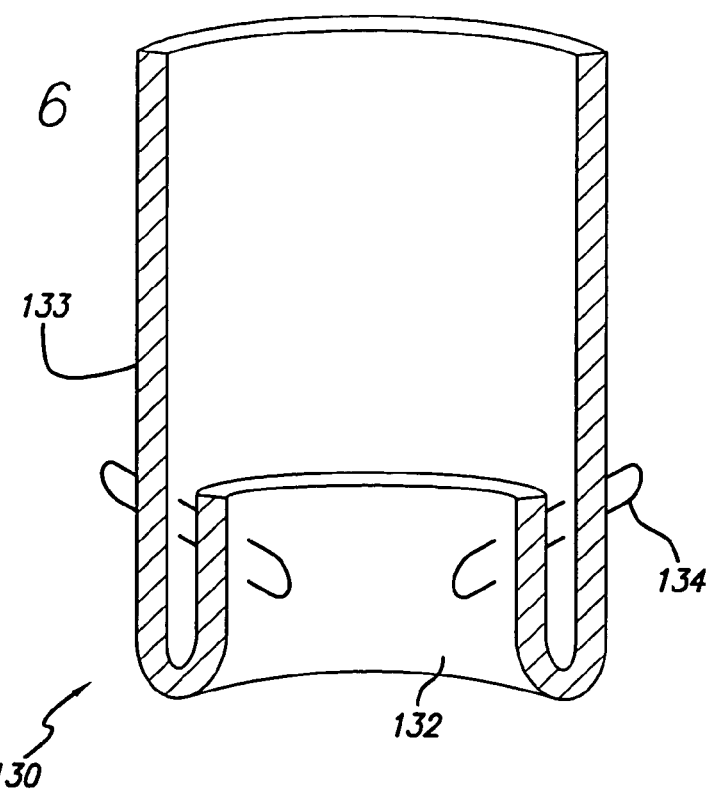
FIG. 6 is a cross-sectional view, depicting a second embodiment of mating structure of a component of a graft device of the present invention.
Figure 7:
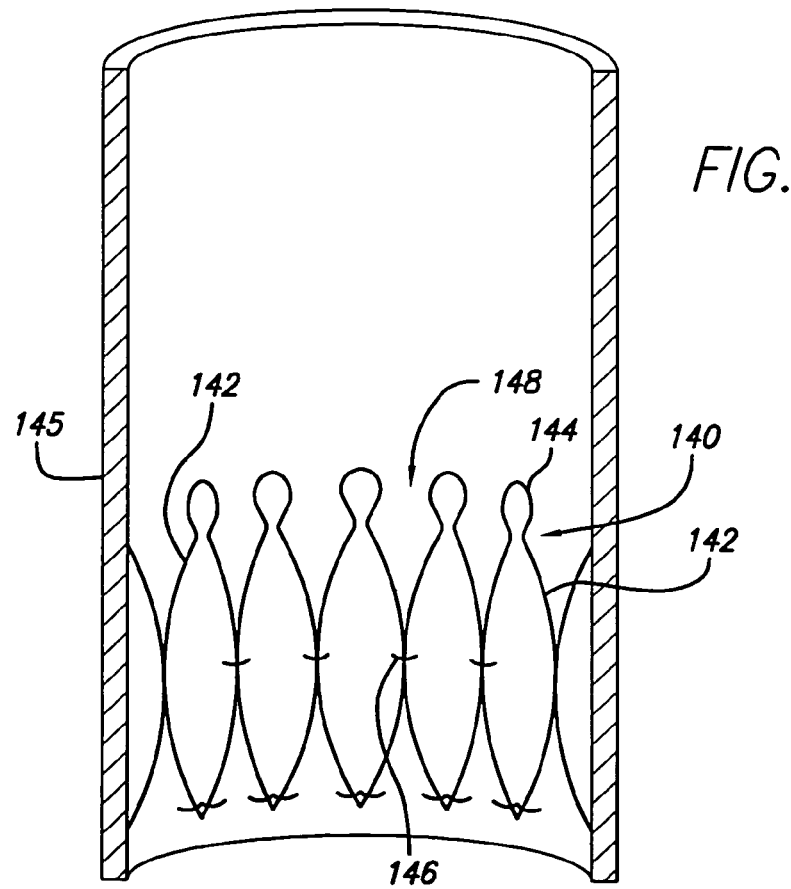
FIG. 7 is a cross-sectional view, depicting a third embodiment of mating structure of a component of a graft device of the present invention.

Turning now to FIGS. 5-7, there is shown various mating structures for mating or connecting one portion of one graft component to another graft component. With reference to FIG. 5, a first embodiment of mating structure 120 includes a suture 122 that is configured about an interior circumference of a graft component 123. The suture 122 is configured into a plurality of loops 124 by connecting multiple point locations thereof to the graft component 123 by any suitable means such as rings or other suture material 126. Although the suture 122 is shown routed about an interior of the graft component 123, it can likewise be attached to an exterior thereof. In either case, the mating structure 120 is adapted to engage a framework extending radially outwardly from another graft component.

A similar approach is shown in FIGS. 6 and 7. The mating structure 130 depicted in FIG. 6 embodies a circumferential fold 132 formed in a graft component 133, the fold 132 being held in place with clips or sutures 134 or any other equivalent means.

As shown in FIG. 7, the mating structure 140 can be defined by a framework 142 having opposing or alternating apices 144 and can be affixed to an interior (or exterior, as needed) circumference of a graft component 145 by sutures or equivalent structure 146. In one aspect, the apices 144 at a superior end 148 of the support structures 140 are intended to extend slightly radially inwardly so that a suitable engaging surface is provided. It is to be recognized that various forms of framework can be employed as such a mating structure provided the desired mating function is accomplished.

Moreover, the mating of two components of a modular graft can be accomplished through the frictional engagement of an outer circumference of one component with an inner circumference of another component. Such a frictional engagement can rely on surface irregularities or other more defined projections or can employ adhesives. It is also contemplated that structures such as that depicted in FIGS. 2 and 3 can be used to join two components. The wall engaging members 86, 98 of those structures 80, 90 are contemplated to lock the components together by penetrating the walls defining the components being joined. The expansion of the structures 80, 90 also ad in maintaining a sealed connection.

Figure 8:
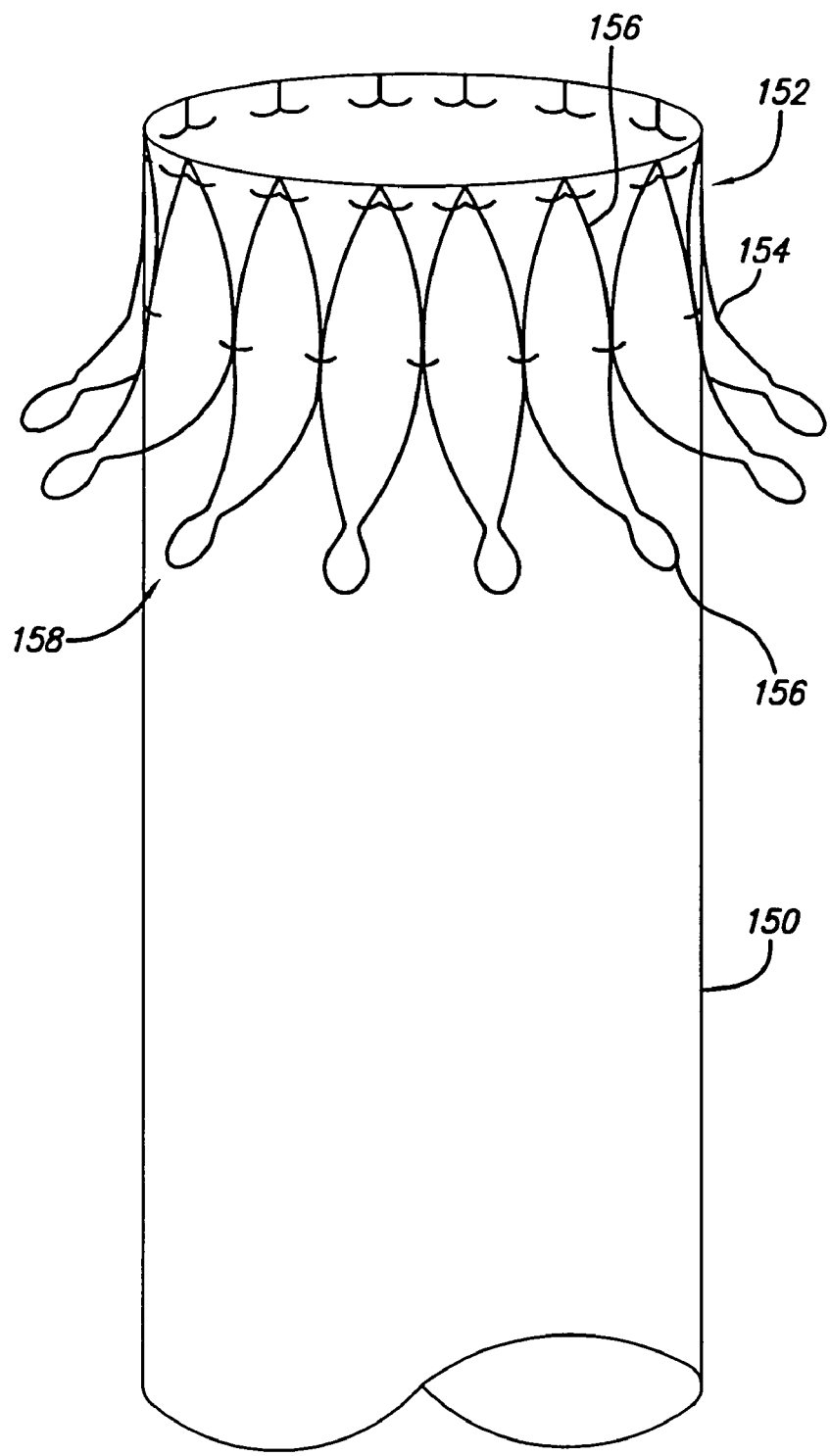
FIG. 8 is a perspective view, depicting one embodiment of grappling or corresponding mating structure attached to a component of the graft device of the present invention.

As shown in FIG. 8, a typical extension component 150 can embody a generally tubular shape. However, it is also contemplated that a limb component can also be bifurcated or trifurcated. The extension components can be made of any suitable conventional material. In one preferred embodiment, the extension components are made of PRFE.

A mating end 152 of a typical extension component is provided with some form of projection or grappling mechanism for engaging the corresponding mating structure of another graft component. In FIG. 8, there is shown one embodiment of an acceptable grappling or mating structure 154, although various other forms are possible. The mating structure 154 can include a self-expanding or balloon expandable framework defined by opposing apices 156 and can be attached to a graft component 150 by conventional methods such as suturing. One end 158 of the mating structure 154 embodies apices 156 which project radially outwardly from and around the outer circumference of the graft component 150. Such structure can alternatively be placed about an interior circumference for a particular application. Being so configured, the extension component can be placed within or about another graft component so that the corresponding mating structures are placed beyond each other and then the components can be moved relative to each other so that they overlap and sealingly engage.

One application of the present invention is to treat or repair diseased vasculature involving the aortic arch (See FIGS. 9-12). Since such vasculature varies from patient to patient, an attempt to mimic the nature vessel anatomy is not made. Rather, the graft device of the present invention is assembled in-situ in a manner to maintain blood flow through the various branches of the anatomy by extending graft conduits from a main component to the necessary locations. Blood thereby flows through the graft device rather than through the diseased vasculature.

Figure 9:
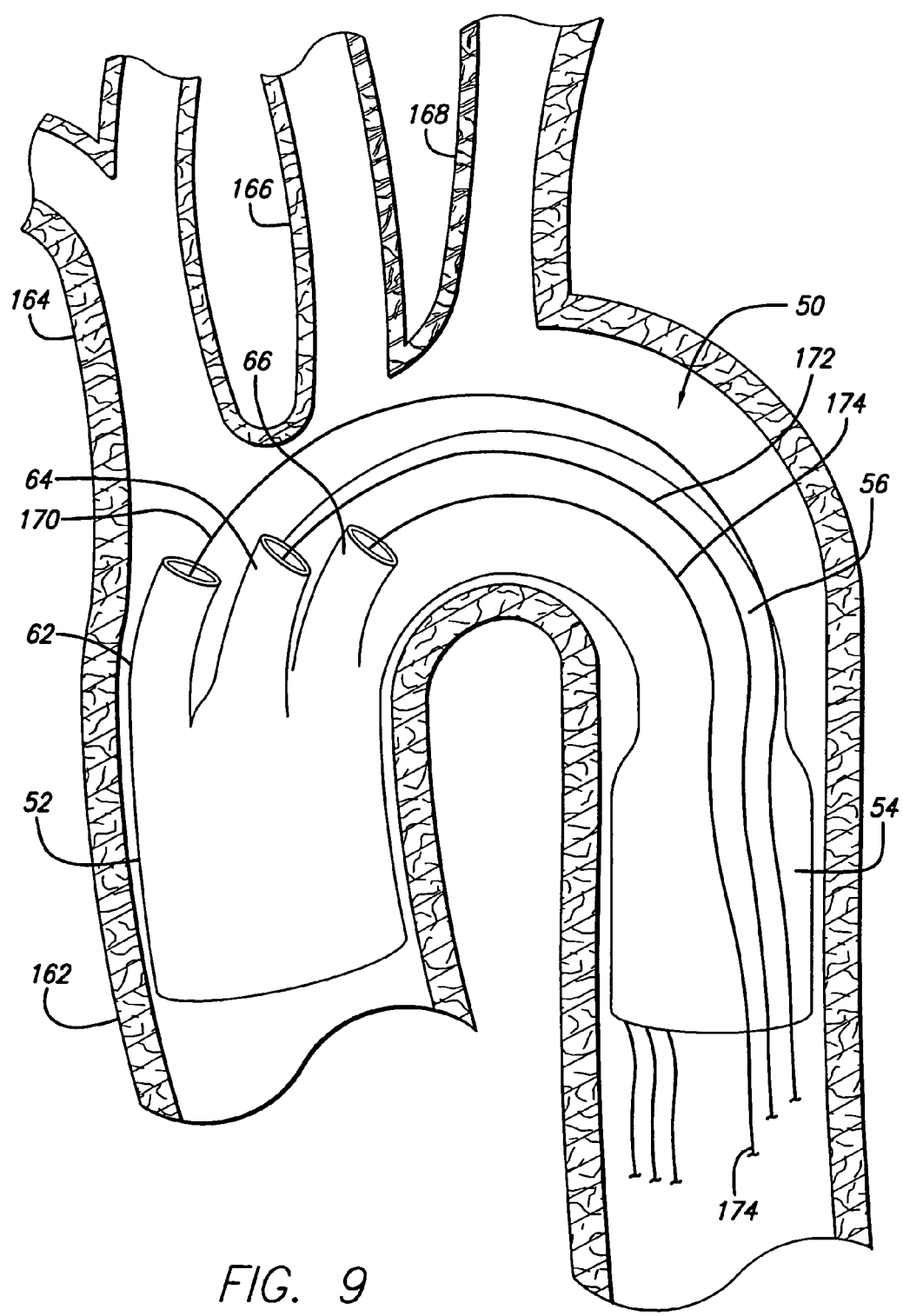
FIG. 9 is a partial cross-sectional view, depicting a first stage of deployment of a graft device of the present invention within vasculature.
Figure 10:
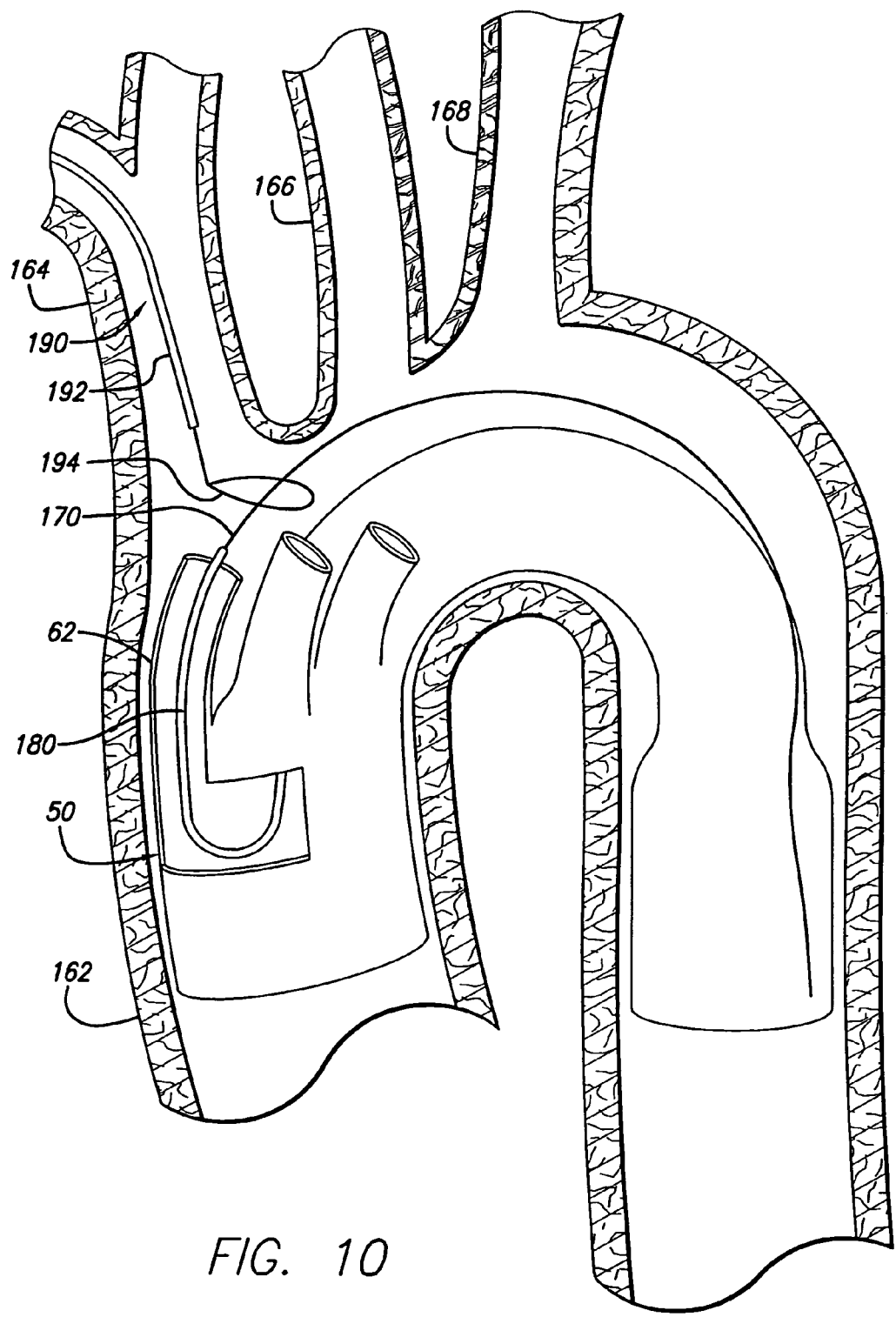
FIG. 10 is a partial cross-sectional view, depicting a first stage of deployment of a graft device of the present invention within vasculature.
Figure 11:
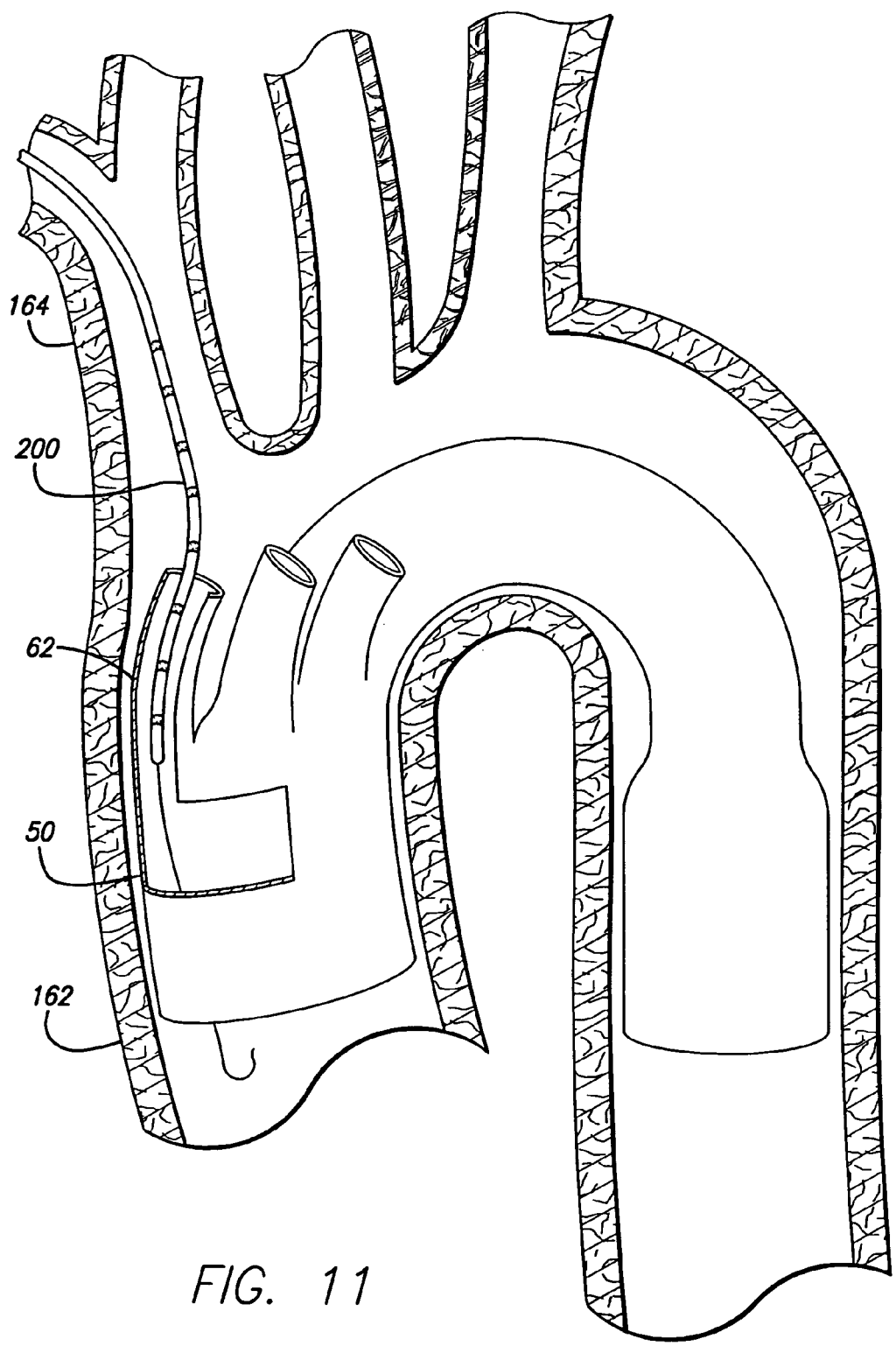
FIG. 11 is a partial cross-sectional view, depicting a third stage of deployment of a graft device of the present invention within vasculature.

For example, the widest or superior portion 52 of the generally bone-shaped main graft or primary stent-graft component 50 is attached to the proximal aorta 162 (FIG. 9). Typically, the main graft component 50 has a diameter of 3.5-4.5 cm at the superior end 52, 2.5-3.5 cm at the inferior portion 54 and about 2 cm at the midsection 56. All branches or limbs 62, 64, 66 of the main component 50 have a diameter of about 1 cm and originate at a point proximal (closer to the heart) to the branches 164, 166, 168 of the aorta 162 to be treated. The origin of the limbs 62, 64, 66 can be staggered at about a 1 cm interval as shown in FIG. 9 or can originate generally at the same longitudinal location. Where the objective is to treat the aortic arch, for example, the relatively narrow midsection 56 provides a space for the various limbs 62, 64, 66 as well as a space for blood flow during the implant procedure, thereby providing continuous perfusion of blood to vital organs and the innominate (brachiocephalic) artery 164, the left carotid artery 166 and the subclavian artery 168.

In order to deliver the main component 50 within the aortic arch 162, a conventional delivery catheter (not shown) can be employed. Such a delivery catheter will embody a device or structure for accomplishing relative movement between the main component and the delivery catheter and deployment of the main component from the catheter such as withdrawing a jacket from over the device. It is also desirable to take a femoral approach and to advance the assembly over a guidewire and through branch arteries to reach the aortic arch.

In one preferred method, the delivery system involves a plurality of guidewires 170, 172, 174. The catheter (not shown) retaining the main component 80 is advanced over the guidewires 170, 172, 174, each of which are individually routed through the interior end 54 of the main graft component 50 and out one limb 164, 166, 168. Deployment involves the attachment of an anchoring device such as those shown in FIGS. 2 and 3 which is affixed to the superior portion 52 of the main component 50. Thereafter, a catheter 180 is advanced over a first guidewire 170. The guidewire 170 is then withdrawn and directed with the aid of the catheter 180 proximate to the proximal branch artery 164. Contemporaneously, a small end hole device 190 embodying an outer sheath 192 and a looped grasping terminal end 194 is placed within the patient's body through a peripheral artery and advanced to within and beyond the proximal branch artery 164 into the aortic arch 162.

Through relative movement between the looped terminal end 194 and the sheath 192 of the snare device 190, the looped terminal end 194 is placed in a position to grasp the first guidewire 170. After grasping the guidewire 170, it is used to insert a calibrated catheter 200 into the proximal aorta 162 through the first limb 62 (See FIG. 11). The calibrated catheter is utilized to select a suitably sized limb extension for mating with the main component 50.

Figure 12:
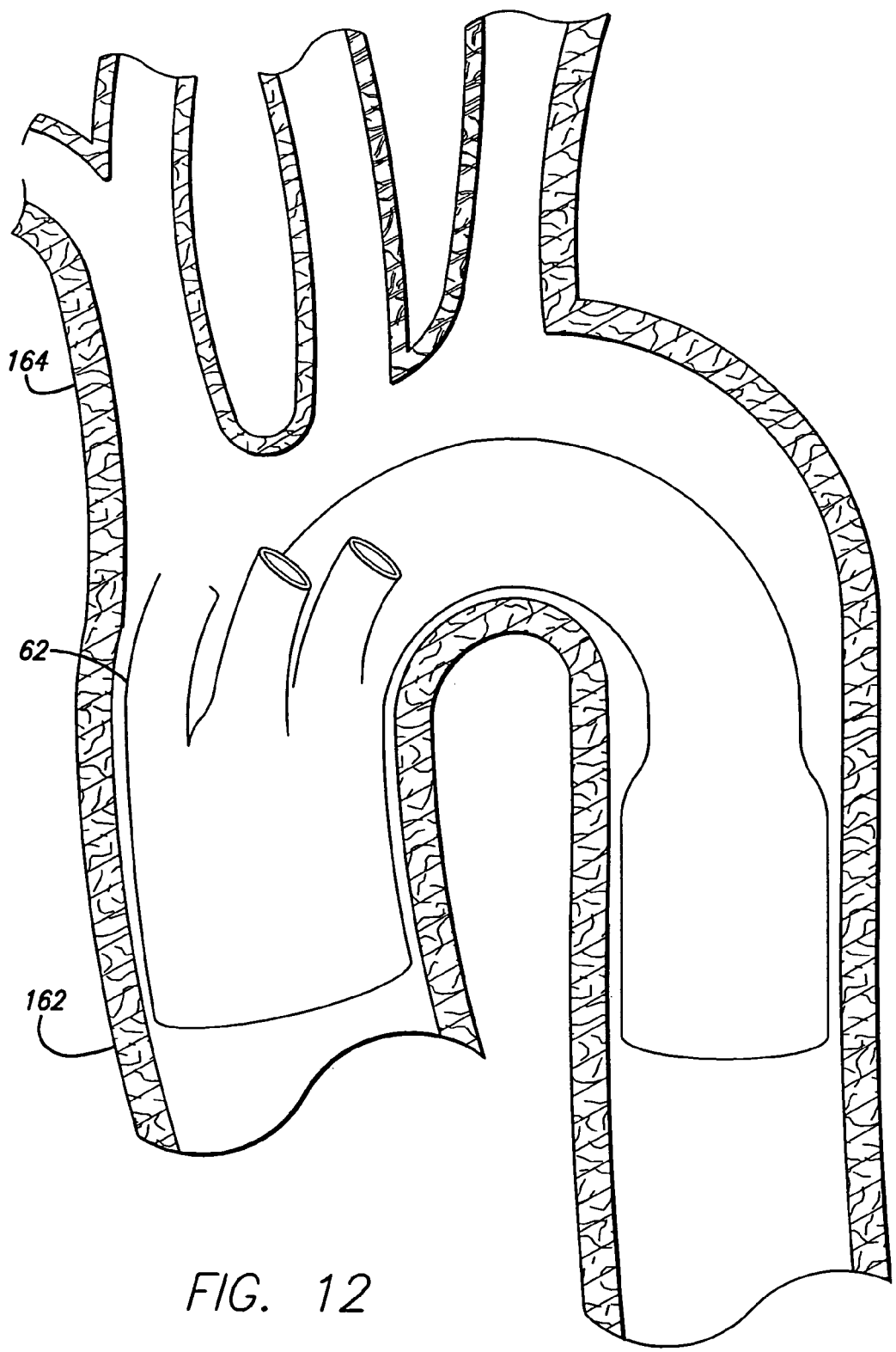
FIG. 12 is a partial cross-sectional view, depicting a fourth stage of deployment of a graft device of the present invention within vasculature.

Next, the calibrated catheter 200 is exchanged (over the wire) for an extension component delivery system 210 which is adapted to retain an extension component 220 in a compressed state as well as with structures for accomplishing relative longitudinal movement therebetween (See FIG. 12). Mating or sealing of a superior or proximal end 222 of the limb extension 220 is accomplished through the engagement between grappling structures such as that shown in FIG. 8 attached thereto with mating structures such as those shown in FIGS. 5-7 which are attached to an interior circumference of the first limb 62. The inferior or distal end 224 of the extension component 220 is equipped with anchoring devices such as those shown in FIGS. 2 and 3. The expansion of the anchoring devices accomplishes the affixation of the limb component 220 to the first branch artery 164.

A similar procedure is employed to attach limb extension to the second 64 and third 66 limbs of the main graft component 50. Additionally, similar mating and grappling and anchoring devices are used to assemble the graft device in-situ. As stated previously, each of the components of the modular graft assembly can include support structures extending a portion or entire length thereof to provide a desired flexibility and radial strength. The graft assembly can also embody the previously described bracing devices. The limb extensions themselves are designed to have a length of approximately 2-3 cm sized to match the 1 cm diameter of the limbs of the graft, whereas the rest of the length thereof matches the diameter of the particular branch artery.

The superior end portion 54 (See FIG. 9) of the main component 50 can be configured with an anchoring device 80, 90 (FIGS. 2, 3) for direct attachment to the aorta. Alternatively, the inferior end portion 54 can be equipped with mating structures 120, 130, 140 (FIGS. 5-7). When equipped with such mating structures 120, 130, 140, a further tubular, bifurcated or trifurcated inferior extension can be mated therewith.

When assembled at the aortic arch, the graft assembly is intended to provide a complex conduit for blood flow. As such, disease occurring at the arch is treated and the vasculature is repaired.

Figure 13:
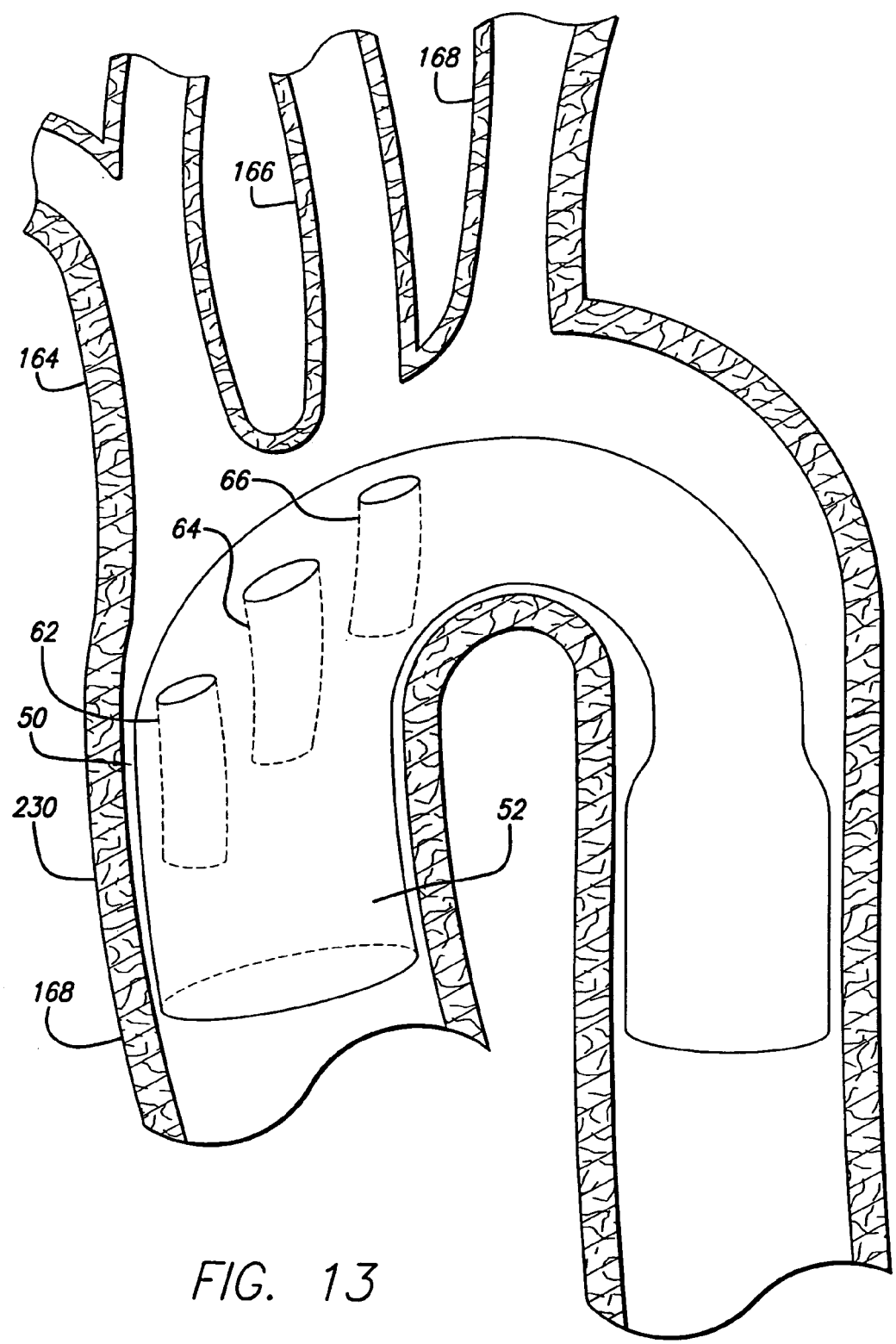
FIG. 13 is a partial cross-sectional view, depicting an alternative embodiment of one component of a graft device of the present invention.
Figure 14:
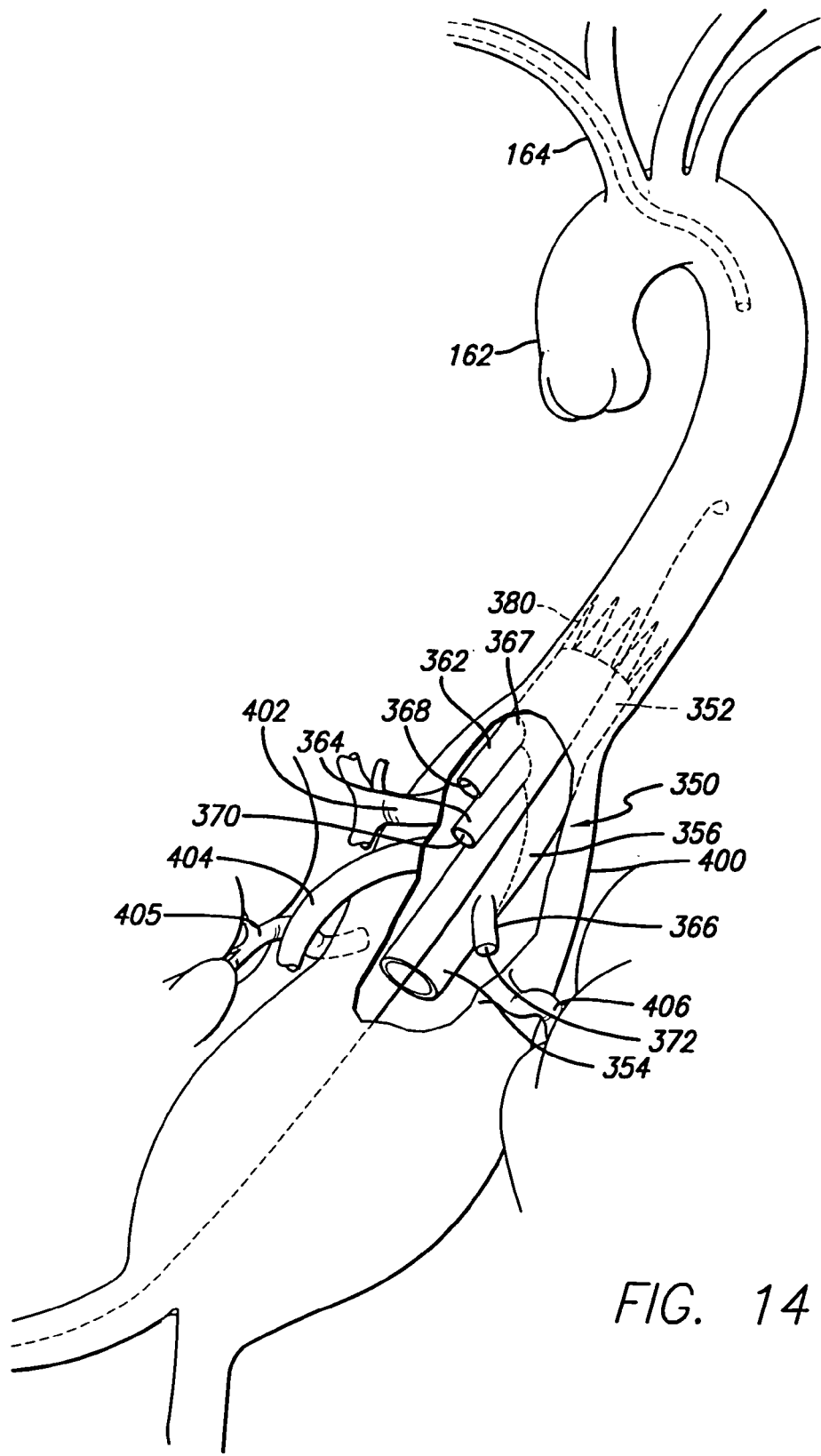
FIG. 14 depicts a first stage in deployment of another embodiment of a component of the graft device of the present invention.

In certain situations, the ascending aorta 230 is less than 6 cm in length thereby leaving insufficient room to both anchor the superior end portion 52 of the main component upstream of a first or proximal branch 164 and provide space for the limbs 62, 64, 66 (FIG. 13). In order to avoid compromising the sealing and anchoring of the superior end portion 52, the limbs can be invaginated to provide an internal docking site for limb extensions. The mating structures can be rearranged as necessary and the limbs can be supported or braced as necessary to accomplish sufficient sealing between graft components.

As stated, the present invention can be applied to various complex vasculatures throughout a patient's body. For example, the present invention can be used to treat aneurysms or stenoses found in the iliac, SMA, SFA or renal arteries. Moreover, aneurysms found in the thoracic region of the aorta are now treatable using the repair system of the present invention.

If left untreated, a thoracoabdominal aortic aneurysm (TAAA) is associated with reduced life expectancy from ruptures. Open surgical aneurysm repair eliminates the risk of ruptures at the expense of high mortality and morbidity rates. Despite obvious advantages over the current alternatives, endovascular repair of TAAA is feasible only if flow can be maintained to all the vital branches of the proximal abdominal aorta, while redirecting flow away from the aneurysm.

The use of multi-limbed unibody grafts to repair TAAA have potential problems. The relative orientation of the graft limbs reflects the relative origination of the guiding catheters employed to deliver the graft to the repair site. If the catheters twist around one another on their way from the femoral artery to the aorta, the branches of the unibody graft do as well. In addition, once such a graft is deployed, visceral perfusion depends on branch deployment and any delay thereof produces ischemia.

In order to determine the feasibility of endovascular repair of TAAA, CT and calibrated catheter angiography are employed. Measurements and the mapping of the target anatomy are taken and recorded. Graft components can then be assembled and sizes selected as necessary to be later used in a repair procedure.

It is contemplated that TAAA repair involves prolonged periods of magnified high resolution imaging, during which the field ranges back and forth from the neck to the groin of the patient, while the view ranges from full left lateral to full right lateral and every angle therebetween. The patient lies in a supine position under general endotracheal anesthesia. Arterial access is obtained through the femoro-brachial arteries by making oblique incisions, although longitudinal incisions can also be made. Heparin is given intravenously to maintain the activated clotting time at twice control from arterial puncture to arterial repair. In addition, heparinized saline is infused slowly through all individual sheaths used during the implant procedure and evoked potentials are continuously monitored. If there is a noticeable change, cerebral spinal fluid (CSF) is drained through a lumbar catheter and blood pressure can be supported pharmacologically to improve spinal perfusion.

With reference to FIGS. 14-22, various steps in treating or repairing a TAAA is described. As shown in FIG. 13, similar to the previously described graft devices, a main component 350 used in treating a TAAA embodies a superior end portion 352, an inferior end portion 354, and a midsection 356, as well as a plurality of limbs 362, 364, 365, 366. As before, the main component 350 is made from conventional fabric. An oblique anastomotic line joins the superior portion 352 to the limbs 362, 364, 365, 366 and inferior end portion 354. The limbs 362, 364, 365 and 366 are staggered longitudinally along the main component 350 an the midsection is tapered with respect to the superior end portion 352 to provide space for the limb. The inferior end portion 354 can have a much smaller diameter to provide space for mating with limb extensions.

The diameters of the various parts of the main component depend on the anatomy of the vasculature being repaired. For instance, the overall diameter is oversized 4-6 mm more than the thoracic aortic implantation site whereas the limbs have diameters approximating the aortic branches and the distal lumen is 20 mm in diameter. Moreover, the length of the main or first component 350 varies according to the extent of involvement of the descending thoracic aortic 400. It is contemplated that there be about a 2.5 cm overlap with healthy proximal aorta and the main component 350, 2 cm overlap between side branches 402, 404, 405, 406 and extension components (described below) and 1-2 cm gap between terminal ends of the limbs 362, 364, 365, 366 and the side branches 402, 404, 405, 406. The shorter the gap the more difficult it can be to accommodate errors in orientation. However, the longer the gap, the greater the risk that an extension component will blow out leading to kinking or dislocation and failure. Moreover, if a limb is below a corresponding branch artery, it is very difficult to add an extension component. Accordingly, pre-sizing is of utmost concern.

An anchoring device 380, which can take various forms such as shown in FIGS. 2, 3 and 13, is affixed to a terminal end of the superior end portion 352. The main or first component 350 can be fully supported, including the limbs, with the structures previously described or many include one or more discrete support structures placed therealong. Such structures can be placed about an outer circumference or inner circumference of the graft. The limbs can be unsupported except at their ends initially and then support structures can be placed in them later. Moreover, each of the four limbs 362, 364, 365, 366 (See FIG. 18 for limb 365 not shown in FIG. 14) can be equipped with mating structures such as those shown in FIGS. 5-7. Additionally, as before, radiopaque rings or markers can be placed along the inside or outside of various components of the graft device of the present invention. These can aid in assembling as well as orientating the graft device within vasculature.

Delivery of the main component 350 within the target site requires a sheath such as a large bore 20-24 French sheath. Any conventional delivery catheter so equipped can be employed. Such conventional catheters may further include an expandable or inflatable member for opening or implanting the support and anchoring devices attached to the main component 350. The delivery catheter is additionally contemplated to include structures or means for accomplishing relative longitudinal movement between the main component 300 and the delivery catheter in order to facilitate deployment and implantation. Conventional guidewires are also contemplated for providing a path taken by any of the delivery catheters used to deploy components of the graft device of the present invention.

In operation, the main component 350 is advanced to a desired level within the thoracic aorta 400 and rotated to align the limbs 362, 364, 365 and 366 with their corresponding branch arteries. A trans-brachial catheter (not shown) can be used for angiographic localization of the branch arteries. The goal is to position the terminal ends of the limbs 362, 364, 365, 366, 1-2 cm above the corresponding branch artery.

With specific reference to FIGS. 15-19, there is shown a preferred procedure for attaching or overlaying a limb extension 452 with a limb 362 of the main or first component 300. As described above, the limb extensions 452 can be fully supported with the devices shown in FIGS. 2-5, 15-22 about an interior or exterior of a particular limb extension 452. The limb extensions are also equipped with grappling or corresponding mating structures (See FIG. 7, for example) configured to engage structures or devices affixed to the limbs 362, 364, 365, 366.

Figure 15:
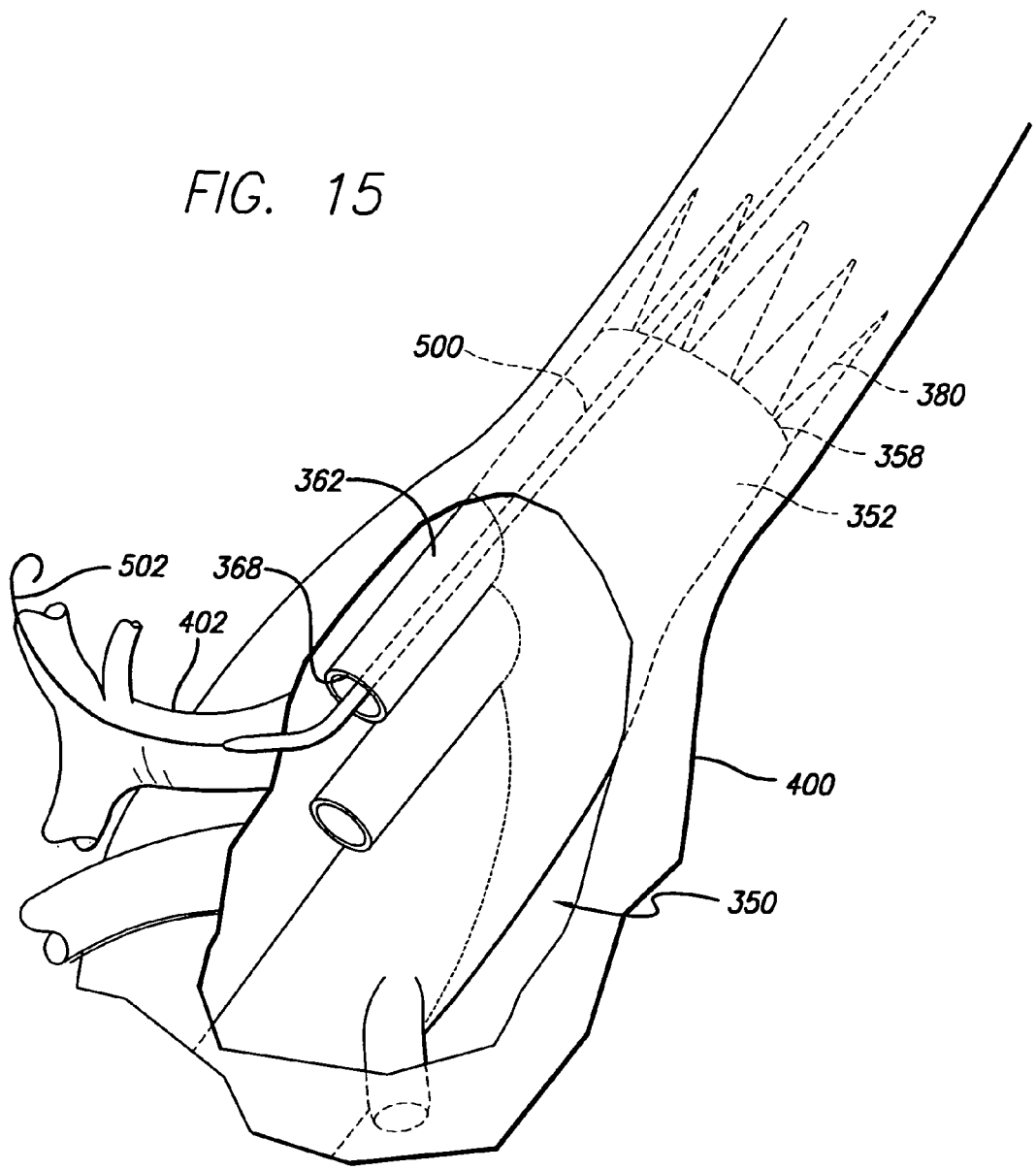
FIG. 15 depicts a second stage in deployment of another embodiment of a component of the graft device of the present invention.

Limb extensions 452 are contemplated to be inserted through a surgically exposed brachial artery, right or left, depending upon the aortic arch anatomy. In theory, right-side access carries a greater risk of stroke, but it sometimes provides a less tortuous route to the descending thoracic aorta 400. As shown in FIG. 15, a guiding catheter 500 is inserted from the brachial artery to the proximal descending thoracic aorta 400. This helps guide the catheter 500 through the aortic arch and minimizes the risk of stroke. The catheter 500 is further positioned through an opening 358 found in the superior end portion 352 of the main component 350 and out an opening or aperture 368 formed in a terminal end of a first limb 362. At this time, a small volume of contrast can be injected to confirm sheath positioning. Depending on the target anatomy, a small radius J-tip catheter 502 can be advanced over a previously placed guidewire and utilized for directing the catheter 500 within the proper branch artery 402, the catheter providing a means of angiography and atraumatic passage into the branch artery. Power injection of full strength contrast (20 ml at 20 ml/s) can be used to more clearly show the anatomy.

Figure 16:
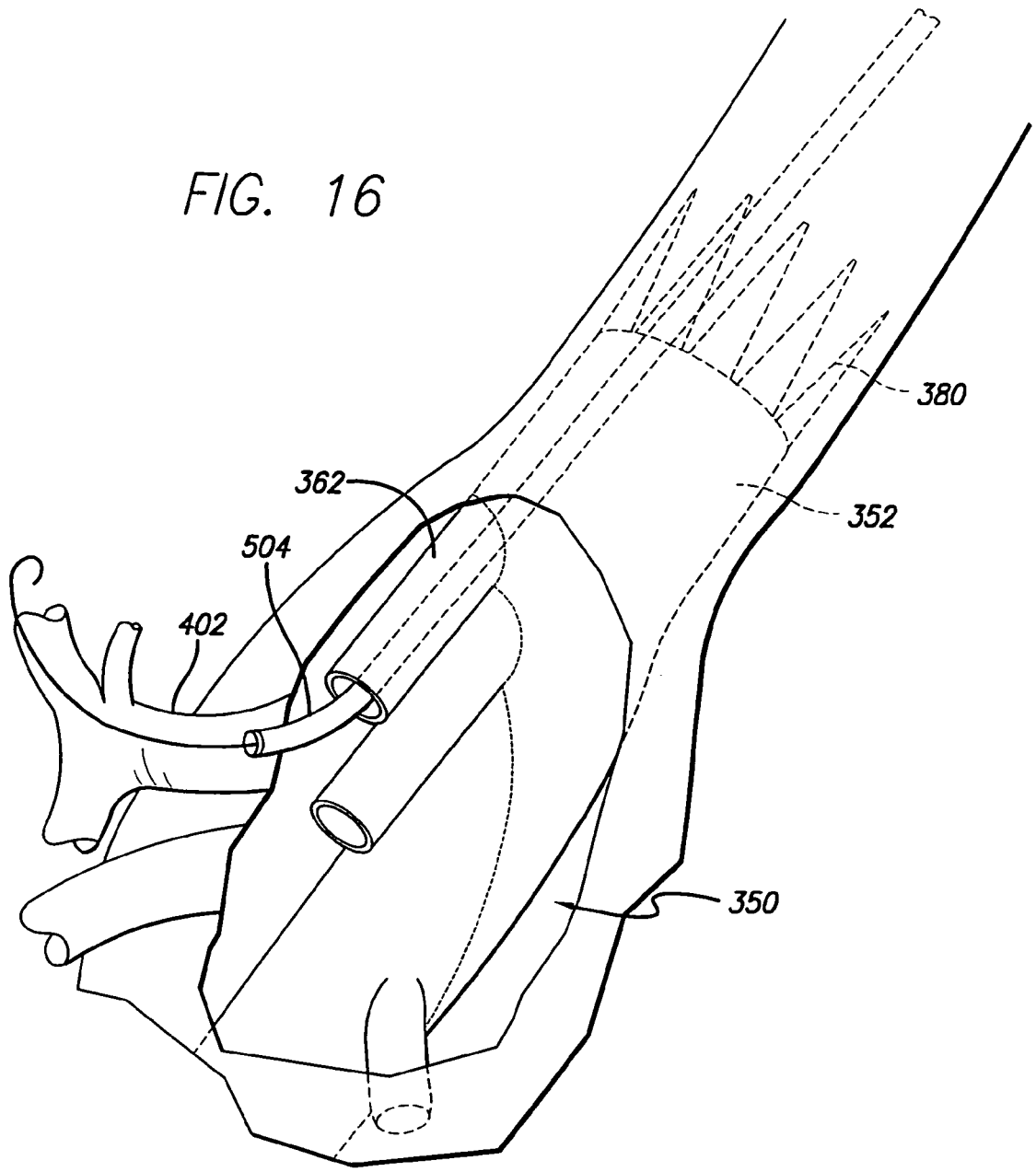
FIG. 16 depicts a third stage in deployment of another embodiment of a component of the graft device of the present invention.
Figure 17:
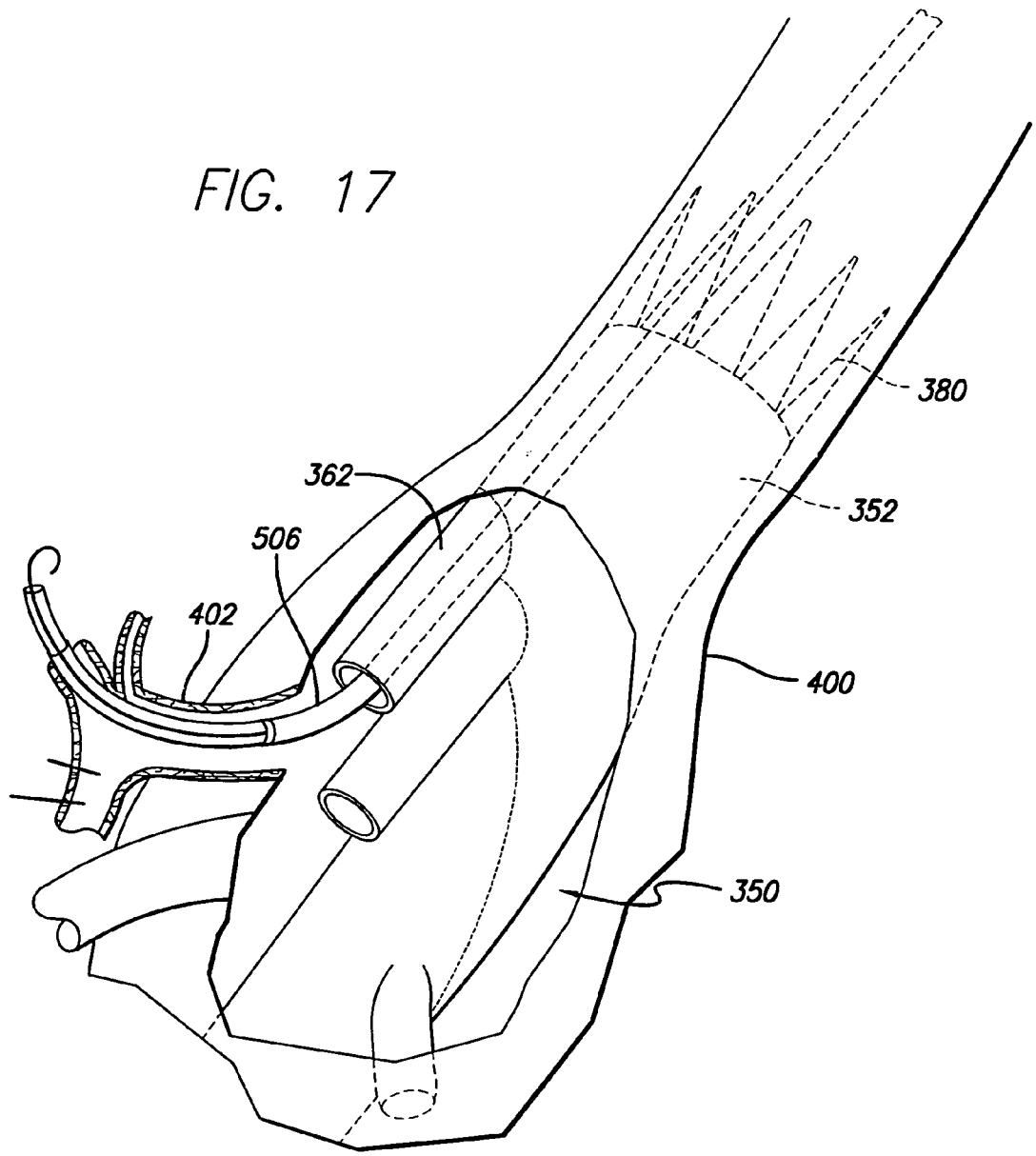
FIG. 17 depicts a fourth stage in deployment of another embodiment of a component of the graft device of the present invention.
Figure 18:
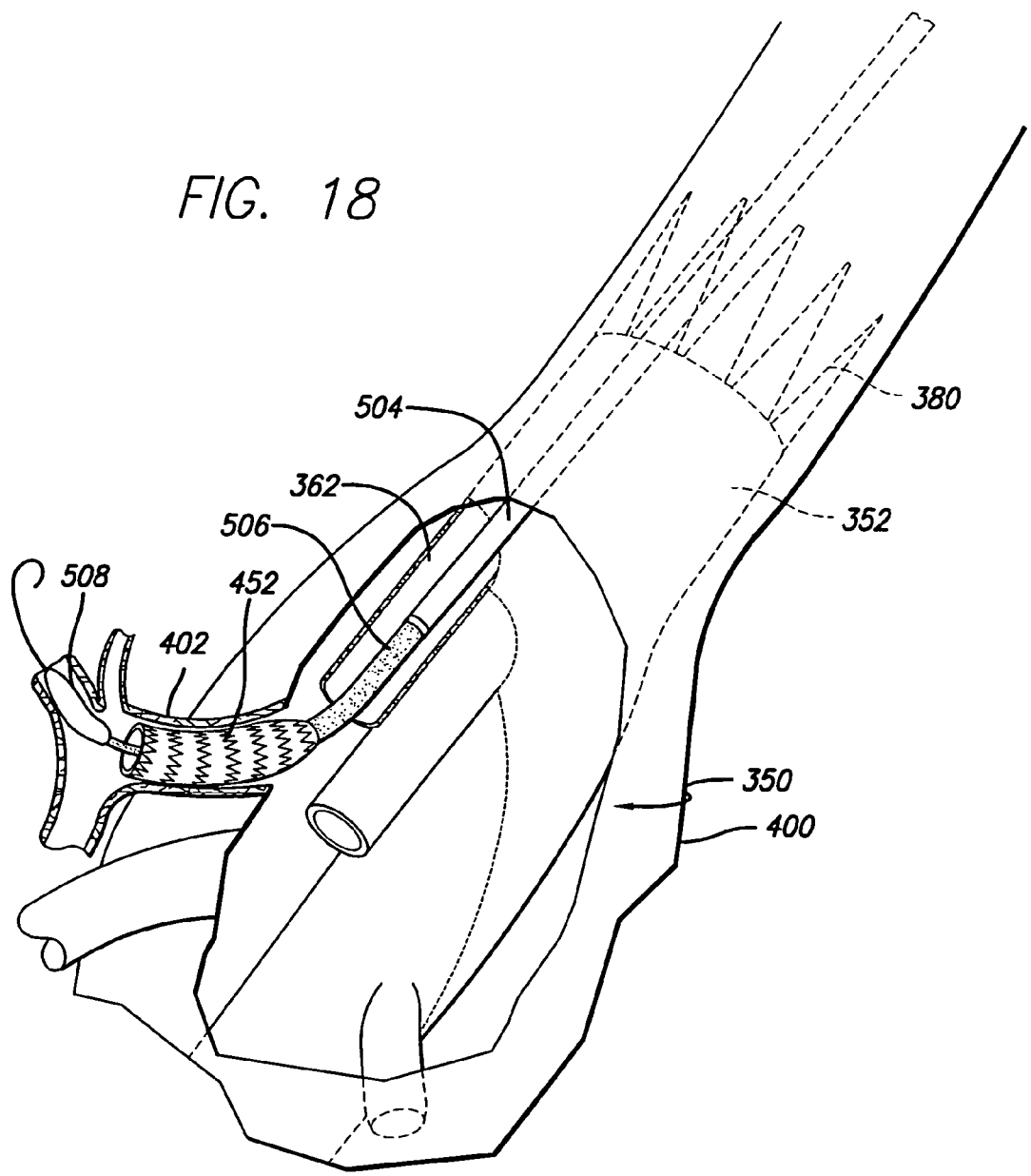
FIG. 18 depicts a fifth stage in deployment of another embodiment of a component of the graft device of the present invention.
Figure 19:
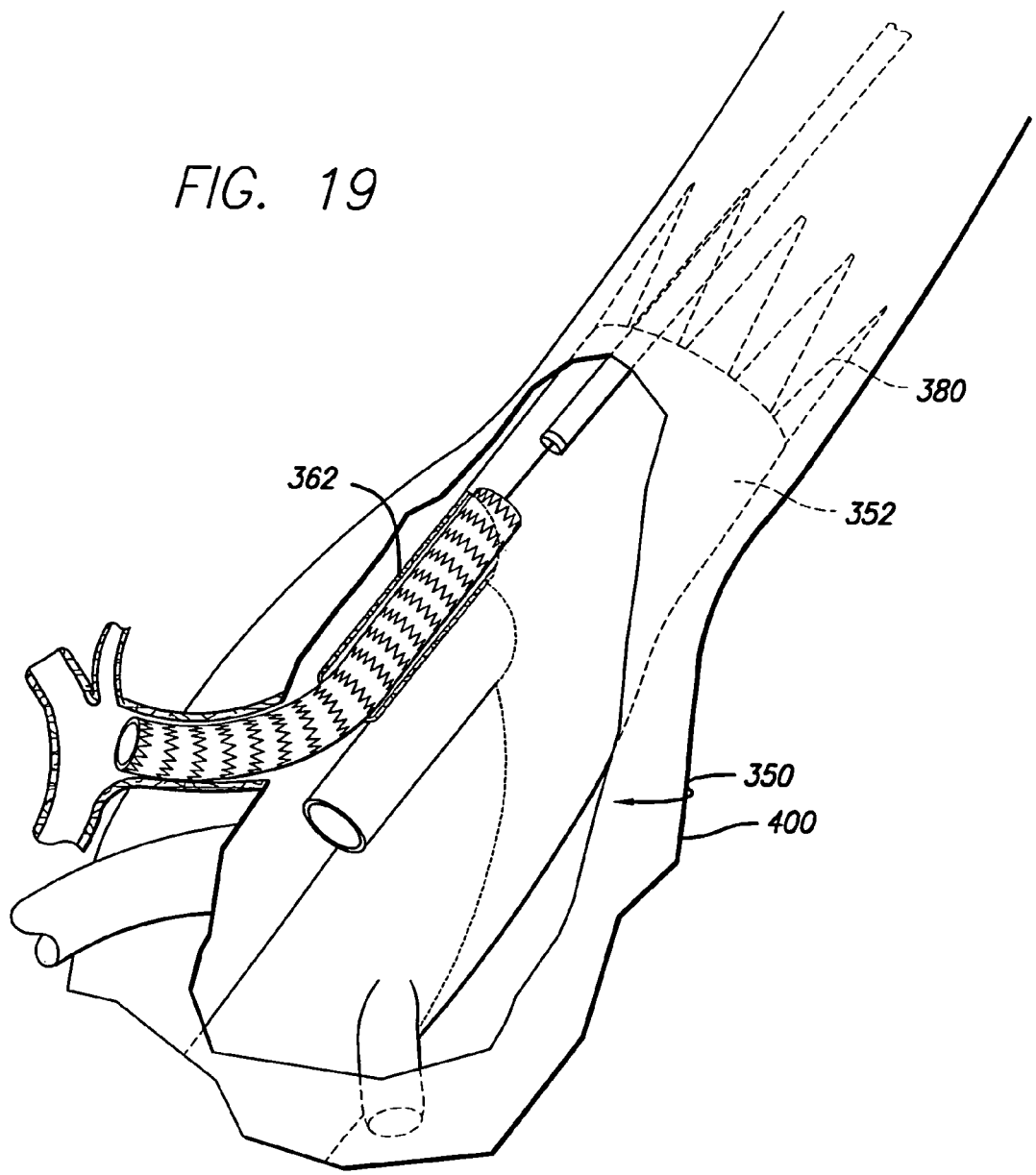
FIG. 19 depicts a sixth stage in deployment of another embodiment of a component of the graft device of the present invention.

The guiding catheter 500 is then replaced with a 12 French endhole sheath 504 (FIG. 16). Next a delivery catheter 506 retaining a limb extension 452 (FIG. 17) is advanced within the sheath 504 and positioned within the target branch artery 402. The delivery catheter 506 is contemplated to be equipped with structure or means, such as a pusher device to accomplish relative longitudinal movement of the catheter and limb extensions 452 and to release the same at the target site (FIGS. 18, 19). The delivery catheter 506 can further include an expandable or inflatable member 508 which is provided to facilitate implantation of the limb extension 452.

Figure 20:
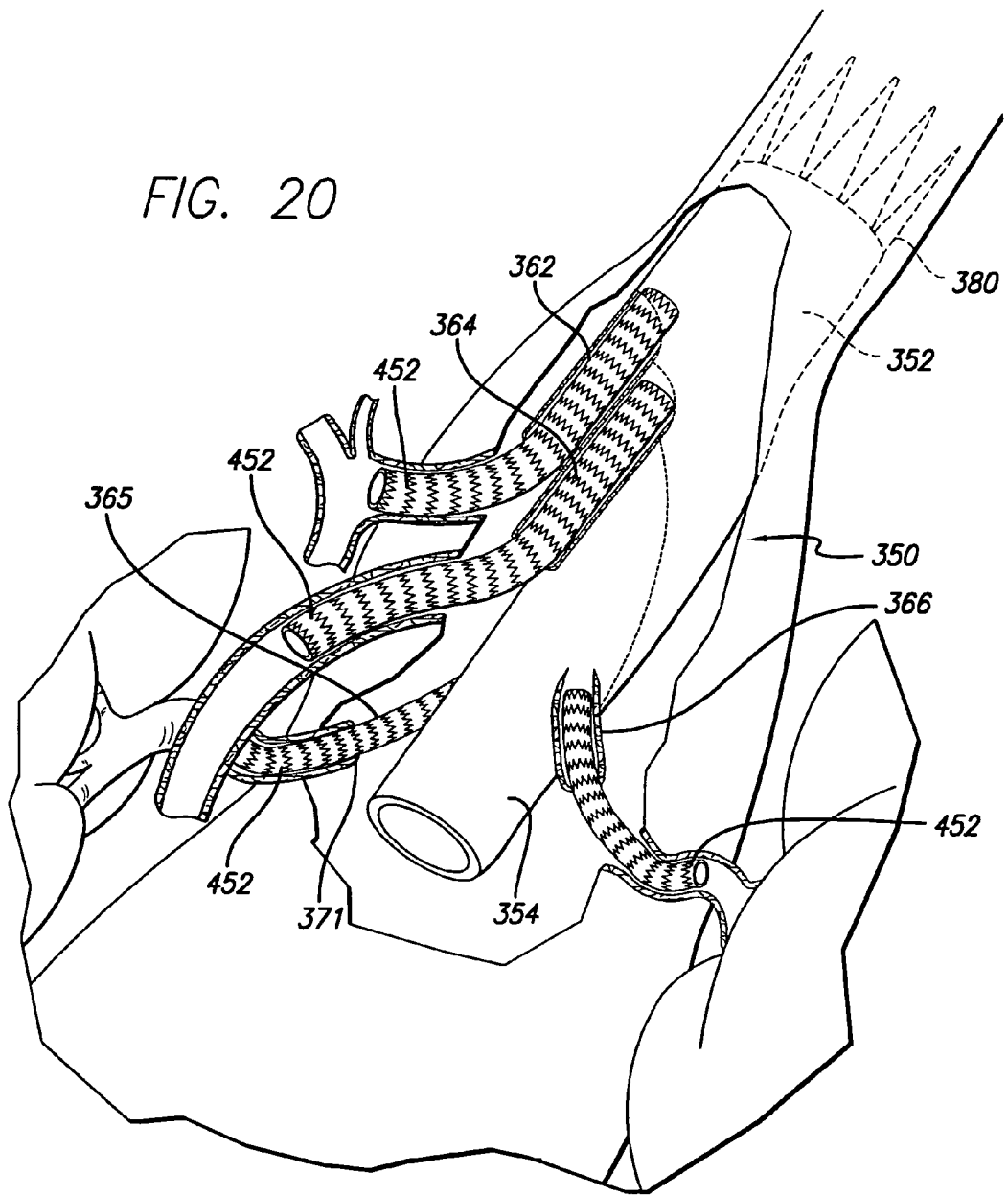
FIG. 20 depicts a seventh stage in deployment of another embodiment of a component of the graft device of the present invention.
Figure 21:
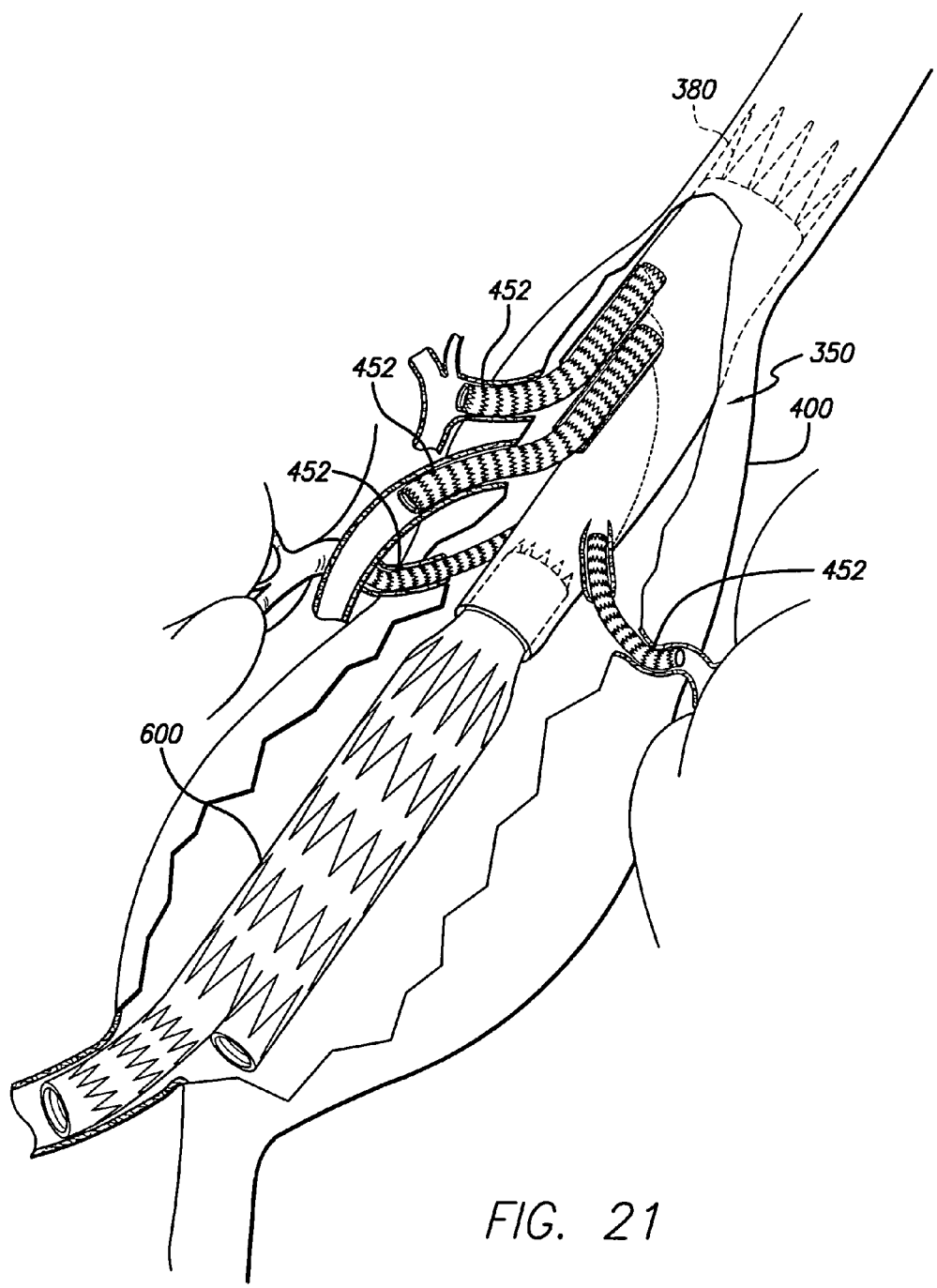
FIG. 21 depicts a eighth stage in deployment of another embodiment of a component of the graft device of the present invention.
Figure 22:
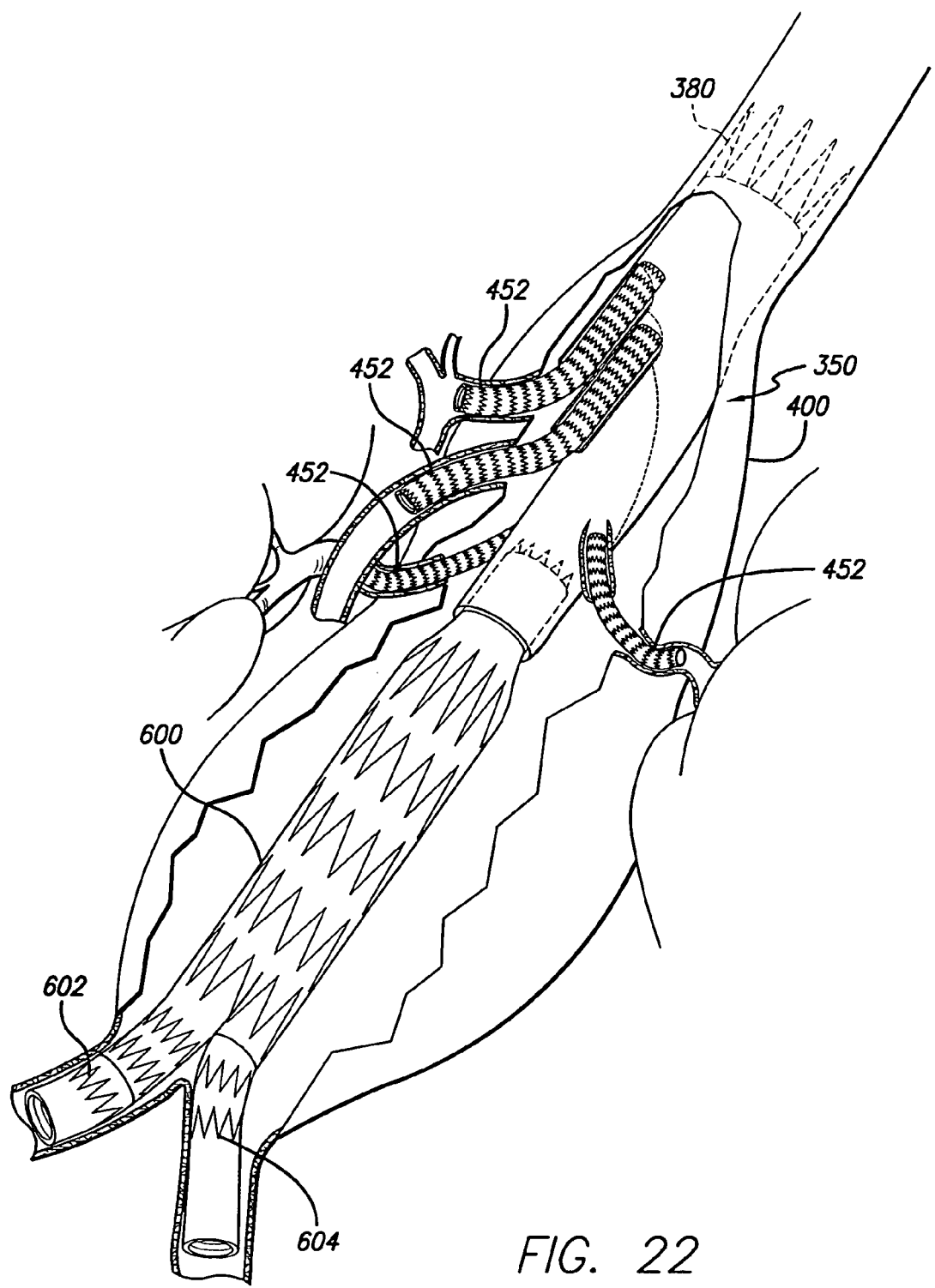
FIG. 22 depicts a ninth stage in deployment of another embodiment of a component of the graft device of the present invention.

The foregoing is repeated until a bridge is provided from the main component to each of the branch arteries (See FIG. 20). The extensions 452 are placed so that there is at least a 2 cm of overlap with both the branch artery and a particular limb of the main component. If this is not feasible using one extension, additional extensions are added, starting distally. Another injection of contrast through the brachial sheath confirms positioning and sealing.

It is recognized that the extensions 452 as well as any other component being joined, can be implanted taking either an inferior or a superior approach. That is, the extensions can be implanted from below the main component 350 or from above as described. Additionally, extender cuffs can be employed to seal a terminal end of the extension within vasculature. The extender cuffs can take on a myriad of forms including an expandable or self-expanding mesh-type frame defined by crossing members, or may embody the attachment or anchoring devices 80, 90 depicted in FIGS. 2 and 3. A simple expandable elastic tube or sleeve or equivalent structures are also suitable.

Finally, a similar procedure is used to advanced, deploy and implant inferior extension components 601, 602, 604 (FIGS. 21, 22) through apertures 370, 371, 372 formed in the other limbs 364, 365, 366 of the main component 350. Such inferior extension components 500, 502, 604 can be tubular or bifurcated depending on the target anatomy and can further include the supporting, anchoring, grappling and mating structures previously described. External structures provide necessary friction for sealing and securing a particular component, although a combination of internal support and anchoring devices are satisfactory as well. Should inferior end extensions not be required, the inferior end portions 354 of the main component 300 can be configured with an anchoring device for direct attachment to the aorta. When completely implanted at the target site, blood flows through the graft device of the present invention which operates to exclude the diseased portion being treated.

Figure 23:
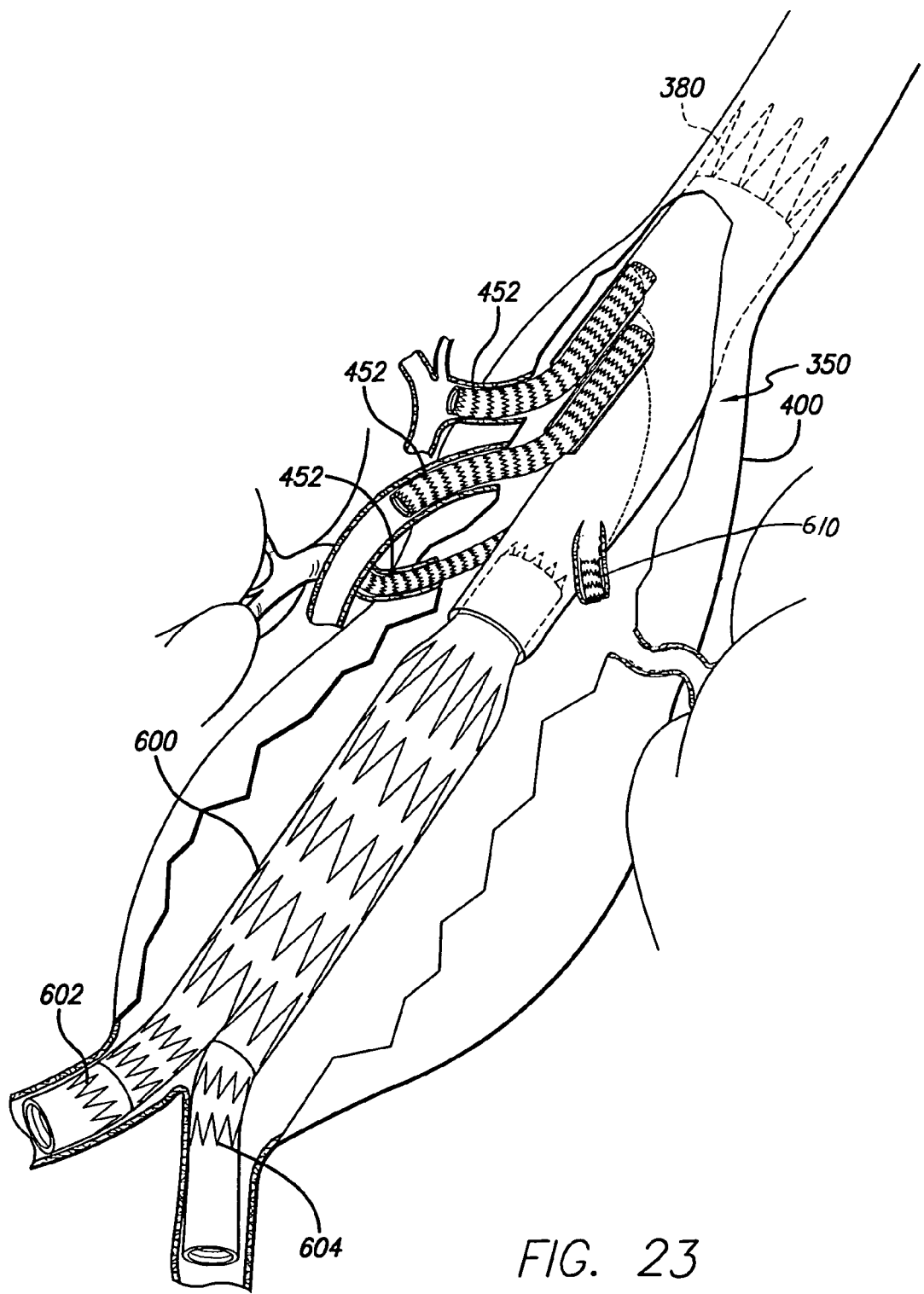
FIG. 23 depicts a graft device of the present invention in combination with an occlusion device.

In the event one or more of the limbs of a graft device are not needed, occlusion of that limb may be desirable. In such an instance, as shown in FIG. 23, for example, one limb can be blocked with an occlusion device 610. Though various forms of an occlusion device are acceptable, such as a windsock design, FIG. 23 depicts an occlusion device 610 that embodies a closed end cuff design that is placed within a particular limb 366. Structures causing a limb to radially contract can also be employed and an elastic band can be used for such a purpose. Of course, any such limb or other portion of the graft device similarly occluded or can be closed shut by suturing prior to use.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A method of treating vasculature having a first vessel in fluid communication with a plurality of vessel portions lying at an angle from the first vessel, the method comprising the steps of:
   configuring a main component including a superior end, an inferior end, and at least four apertures in combination with at least three extension components each oriented in a substantially reverse direction from an aperture at an adjacent superior end or an aperture at an adjacent inferior end, wherein each of the extension components includes a mating end and an anchoring end;
   delivering the main component within the first vessel;
   attaching the superior end of the main component within the first vessel; and
   configuring the mating ends of each of the three extension components into engagement with one of the apertures of the main component oriented in the substantially reverse direction from the aperture at the adjacent superior end or the aperture at the adjacent inferior end.

2. The method of claim 1, further comprising attaching the anchoring ends of each of the extension components to one of the vessel portions lying at the angle from the first vessel.

3. The method of claim 1, further comprising attaching the inferior end of the main component to the first vessel.

4. The method of claim 1, further comprising advancing a delivery catheter along each of a number of guidewires.

5. A method for treating vasculature including a first vessel and a plurality of vessel portions in fluid communication therewith and lying at an angle to the first vessel, comprising:
   configuring a graft device including a superior end, an inferior end, and a midsection having at least three tubular portions extending therefrom, each tubular portion oriented in a substantially reverse direction from an aperture at an adjacent superior end or an aperture at an adjacent inferior end;
   delivering the graft device within the vasculature;
   attaching the superior end of the graft device within the vasculature;
   attaching each of the tubular portions to one of the vessel portions lying at the angle from the first vessel oriented in the substantially reverse direction from the aperture at the adjacent superior end or the aperture at the adjacent inferior end; and
   attaching the inferior end of the graft device to the first vessel.

\* \* \* \* \*